United States Patent
Becker et al.

(10) Patent No.: US 6,559,153 B2
(45) Date of Patent: May 6, 2003

(54) QUINAZOLINE DERIVATIVES AS ALPHA-1 ADRENERGIC ANTAGONISTS

(75) Inventors: Cyrus Kephra Becker, San Francisco, CA (US); Chris Richard Melville, Palo Alto, CA (US); Jürg Roland Pfister, Los Altos, CA (US); Xiaoming Zhang, Campbell, CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/942,385

(22) Filed: Aug. 29, 2001

(65) Prior Publication Data
US 2002/0045614 A1 Apr. 18, 2002

Related U.S. Application Data
(60) Provisional application No. 60/229,503, filed on Aug. 31, 2000.

(51) Int. Cl.$^7$ .................. C07D 401/12; C07D 401/14; A61K 31/517
(52) U.S. Cl. ............... 514/266.22; 514/266.2; 514/266.21; 544/284; 544/291
(58) Field of Search ............... 514/260, 266.22, 514/266.2; 544/291, 284

(56) References Cited

U.S. PATENT DOCUMENTS 6,169,093 B1   1/2001   Fox et al.
6,355,641 B1   3/2002   Coffen

FOREIGN PATENT DOCUMENTS

WO   WO 97/11698   4/1997
WO   WO 97/23462   7/1997

OTHER PUBLICATIONS

Ruffolo et al., PubMed Abstract (Eur. Urol. 36 Suppl 1: 17–22), 1999.*
Martin et al., PubMed Abstract (Eur. Urol. 33 Suppl 2: 12–8), 1998.*
Raskind, et al., "The $\alpha_1$–Adrenergic Antagonist Prazosin Ameliorates Combat Trauma Nightmares in Veterans With Posttraumatic Stress Disorder: A Report of 4 Cases," *Journal Clin. Psychiatry*, (2000), pp. 129–133, 61:2.
Brooks et al., "Interaction of Clozapine and other Antipsychotic Drugs with Human Alpha 1–adrenergic Receptor Subtypes",*Proc. West. Pharmacol. Soc.*, (1999), pp. 67–69, vol. 42.
Acosta–Martinez et al., "Localization of alpha 1B–adrenergic Receptor in Female Rat Brain Regions Involved in Stress and Neuroendocrine Function", *Neurochem. Int.*, (1999) pp. 383–391, vol. 35, Elsevier Science Ltd.

Bakshi et al., "Alpha–1–adrenergic Receptors Mediate Sensorimotor Gating Deficits Produced by Intracerebral Dizocilpine Administration in Rats", *Neuroscience*, (1999), pp. 113–121, vol. 92, Pergamon.

Carasso et al., "Disruption in Prepulse Inhibition after Alpha–1 Adrenoceptor Stimulation in Rats", *Neuropharmacol.*, (1998), pp. 401–404, vol. 37, Pergamon.

Giardina et al., "Synthesis and Biological Profile of the Enantiomers of {4–(4–Amino–6,7–dimethoxyquinazolin–2–yl]–cis–octahydroquinoxalin–1–yl]furan–2–ylmethanone (Cyclazosin), a Potent Competitive $\alpha$1B–Adrenoceptor Antagonist", *J. Med. Chem.*, (1996), pp. 4602–4607:39.

Patane et al., "4–Amino–2–[4–[1–(benzyloxycarbonyl)–2(S)–[[(1,1–dimethylethyl) amino] carbonyl]–piperazinyl]–6,7–dimethoxyquinazoline (L–765,314): A Potent and Selective alpha 1B Adrenergic Receptor Antagonist", *J. Med. Chem*, (1998), pp. 1205–1208, vol. 41, No. 8.

Xie et al, "Increase in alpha 1B Adrenergic Receptor mRNA Expression in the Rat Dorsal Root Ganglion (DRG) after Spinal Nerve Injury", *Soc. for Neuroscience, Abstract*, (1998), p. 2089, vol. 24, Part 2.

Lee et al., "Receptor Subtype Mediating the Adrenergic Sensitivity of Pain Behavior and Ectopic discharges in Neuropathic Lewis Rats", *J. Neurophysiol.*, (1999), pp. 2226–2233, vol. 81, The American Physiological Society.

* cited by examiner

Primary Examiner—Deepak Rao
(74) Attorney, Agent, or Firm—Rohan Peries

(57) ABSTRACT

This invention relates to compounds which are generally alpha-1B adrenergic receptor antagonists and which are represented by Formula (I):

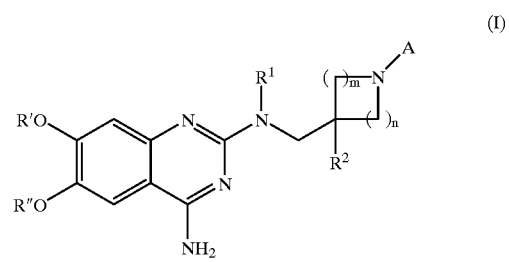

(I)

wherein R', R", $R^1$, $R^2$, m, n, and A are as defined in the specification, or acceptable prodrug, salt or solvate thereof. The invention further relates to pharmaceutical compositions containing such compounds, methods for their use as therapeutic agents, and methods of preparation thereof.

45 Claims, No Drawings

QUINAZOLINE DERIVATIVES AS ALPHA-1 ADRENERGIC ANTAGONISTS

CROSS REFERENCE TO RELATED APPLICATIONS

This Application claims benefit under Title 35 U.S.C. 119(e) of U.S. Provisional Application No. 60/229,503 filed Aug. 31, 2000; hereby incorporated as reference in its entirety.

FIELD OF THE INVENTION

The present invention relates to quinazoline derivatives that are alpha-1 adrenergic receptor antagonists, and in particular to certain quinazoline derivatives that are selective alpha-1B adrenergic receptor antagonists, and associated pharmaceutical compositions, methods for use as therapeutic agents, and methods of preparation thereof.

BACKGROUND OF THE INVENTION

Alpha-1 adrenergic receptors are G-protein coupled transmembrane receptors that mediate various actions of the sympathetic nervous system through the binding of the catecholamines, epinephrine and norepinephrine. Currently, several subtypes of the alpha-1 adrenergic receptors are known to exist for which the genes have been cloned: alpha-1A (previously known as alpha-1C), alpha-1B and alpha-1D. The existence of an additional subtype, the alpha-1L adrenergic receptor subtype, has been proposed; however, the gene for the alpha-1L adrenergic receptor subtype has yet to be cloned. Although these subtypes can be pharmacologically distinguished, existing subtype-selective compounds are only moderately specific and may interact with more than one alpha-1 adrenergic receptor subtype (See Giardina, D., et al., *J. Med. Chem.*, 1996, 39:4602–4607).

Non-selective alpha-1 adrenoceptor antagonists have been used to treat lower urinary tract symptoms associated with benign prostatic hyperplasia (BPH). Further, alpha-1 adrenoceptor antagonists can be effective in reducing or alleviating urinary tract disorders and/or symptoms thereof, such as pelvic hypersensitivity, overactive bladder, urinary frequency, nocturia, urinary urgency, detrusor hyperreflexia, outlet obstruction, prostatitis, incontinence, urge incontinence, urethritis, prostatodynia, idiopathic bladder hypersensitivity, and the like. Accordingly, therapeutic use of nonselective alpha-1 adrenergic receptor antagonists must be carefully monitored as such antagonists can produce significant undesirable side effects such as postural hypotension, sedation or depression, increased gastrointestinal motility and diarrhea, impaired ability to ejaculate, nasal stuffiness, akinesia and the like.

Compounds that interact more selectively with a particular alpha-1 adrenergic receptor subtype may prove clinically useful in providing more selective treatment of conditions and diseases associated with abnormal activity at the receptor subtype. For example, alpha-1 adrenergic receptor antagonists that can selectively ameliorate nociceptive and/or neurogenic pain without affecting blood pressure or causing postural hypotension, dizziness or syncope, are desirable.

Selective alpha-1B adrenergic receptor antagonists can also be useful in the treatment of CNS disorders including, but not limited to, anxiety, sleep disorders, and schizophrenia (see, e.g., Bakshi, et al. (1999) *Neuroscience* 92:113–121; Carasso, et al. (1998) *Neuropharmacol.* 37:401–404; and Acosta-Martinez, et al. (1999) *Neurochem. Int.* 35:383–391). Recently, the non-selective alpha-1 adrenergic receptor antagonist prazosin has also been useful in the amelioration of combat trauma nightmares in veterans with posttraumatic stress disorder (see e.g., Raskind, et al. (2000) *J. Clin. Psychiatry* 61(2), 129–133).

Because of their ability to selectively antagonize alpha-1B adrenergic receptors, the compounds of this invention lack the undesirable effects of non-selective alpha-1 adrenergic receptor antagonists such as prazosin, terazosin, and doxazosin.

DESCRIPTION OF THE RELATED ART

U.S. patent application Ser. No. 09/521,185 (Coffen, et al.), refers to certain oxazolone derivatives as alpha-1B adrenergic receptor antagonists.

PCT Application Publication WO97/11698 (assigned to Merck), refers to certain selective alpha-1B adrenergic receptor antagonists used in the treatment of hypertension.

PCT Application Publication WO97/23462 and U.S. Pat. No. 6,169,093 (assigned to Pfizer), refer to certain quinoline and quinazoline compounds useful in the treatment of benign prostatic hyperplasia.

Raskind, et al., *J. Clin. Psychiatry* 2000, 61(2), 129–133, refer to the use of prazosin to ameliorate combat trauma nightmares in veterans with posttraumatic stress disorder.

Brooks, et al., *Proc. West. Pharmacol. Soc.* 1999, 42, 67–69, refer to clozapine and other antipsychotic drugs for interaction with human alpha-1 adrenergic receptor subtypes.

Acosta-Martinez, et al., *Neurochem. Int.* 1999 35:383–391, refer to the localization of alpha-1B adrenergic receptor in female rat brain regions involved in stress and neuroendocrine function.

Bakshi, et al., *Neuroscience* 1999, 92:113–121, refer to alpha-1 adrenergic receptors mediating sensorimotor gating deficits which are thought to result in sensory inundation, cognitive fragmentation and attentional deficits, all of which are features common to schizophrenia and drug-induced psychotic states.

Carasso, et al., *Neuropharmacol.* 1998, 37:401–404, refer to the role of alpha-1 adrenoceptors in the psychotherapeutic actions of certain antipsychotics.

Giardina, et al., *J. Med. Chem.* 1996, 39, 4602–4607, refer to the synthesis of cyclazosin enantiomers and their activity as alpha-1B antagonists.

Patane, et al., *J. Med. Chem,* 1998, 41,1205–1208, refer to L-765314 as a potent and selective alpha-1B antagonist.

Xie, et al., *Soc. for Neuroscience Abstract,* 1998, 24, 2089, refer to certain alpha-1B adrenergic receptor mRNA expression in rat DRG after spinal nerve injury.

Lee, et al., *J. Neurophysiol.* 1999, 81, 2226–2233, refer to certain receptor subtypes mediating the adrenergic sensitivity of pain behavior.

All publications, patents, and patent applications cited herein, whether supra or infra, are each hereby incorporated by reference in its entirety.

SUMMARY OF THE INVENTION

This invention relates to compounds comprising Formula (I):

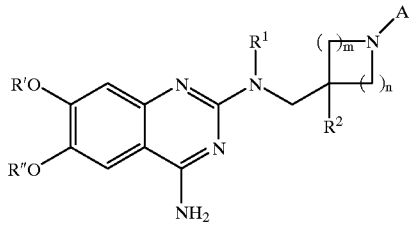

wherein:

- $R^1$ is hydrogen, or lower alkyl;
- $R^2$ is lower alkyl, heterocyclyl, heteroaryl, or aryl, all optionally substituted with lower alkyl, alkoxy, halogen, or cyano;
- R' and R" are each independently lower alkyl;
- A is hydrogen, $-(CH_2)_{0-1}R^3$, $-C(O)R^3$, $-SO_2R^3$, $-C(O)OR^3$, $-C(O)NR^4R^5$, $-SO_2NR^4R^5$, $C(NR^6)R^3$, or $-C(NR^6)NR^4R^5$;
- $R^3$ is independently in each occurrence lower alkyl optionally substituted with halogen, amino, alkylamino, hydroxy, alkoxy, acyloxy, aminocarbonyl, alkoxycarbonylamino, nitro, or cyano; aryl; arylalkyl; heteroaryl; heteroarylalkyl; cycloalkyl; cycloalkylalkyl; heterocyclyl; or heterocyclylalkyl;
- $R^4$ and $R^5$ are each independently hydrogen or $R^3$ as defined above;
- $R^4$ and $R^5$ taken together with the nitrogen to which they are attached form a 5- to 7-membered ring, optionally incorporating one or two additional ring heteroatoms
- $R^6$ is hydrogen, lower alkyl or cyano; and chosen from N, S, or O;
- n is an integer from 0 to 2 inclusive and m is an integer from 0 to 3 inclusive, wherein m+n is equal to or larger than 2;
- or acceptable prodrug, salt or solvate thereof.

In another aspect, the invention relates to pharmaceutical compositions containing a therapeutically effective amount of at least one compound of Formula (I), or acceptable prodrug, salt or solvate thereof, in admixture with at least one suitable carrier.

In another aspect, the invention further relates to a process which comprises reacting a compound having the formula

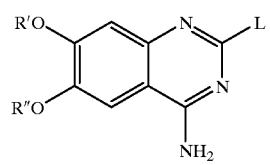

wherein L is a leaving group, with a compound of general formula

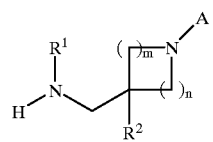

to provide a compound of the general Formula (I)

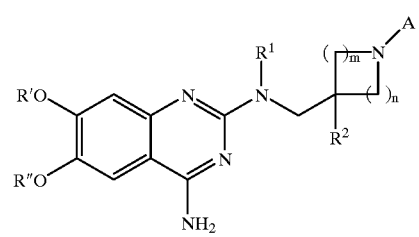

wherein R', R", $R^1$, $R^2$, m, n, and A are as defined herein.

In another embodiment, the invention further relates to a process which comprises reacting a compound having the formula:

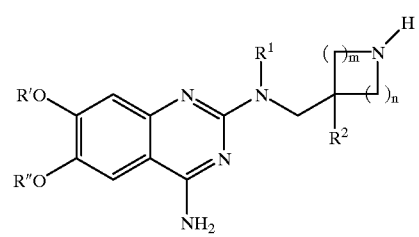

with a compound of the general formula A-L, wherein L is a leaving group, to provide a compound of general Formula (I)

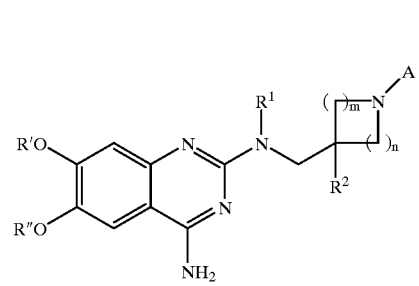

wherein R', R", $R^1$, $R^2$, m, n and A are as defined herein.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a," "an," and "the" include plural referents unless the context clearly dictates otherwise.

"Lower alkyl" means the monovalent linear, branched or cyclic saturated hydrocarbon radical, having from one to six carbon atoms inclusive, unless otherwise indicated. Examples of lower alkyl radicals include, but are not limited to, methyl, ethyl, propyl, isopropyl, sec-butyl, tert-butyl, n-butyl, n-pentyl, n-hexyl, cyclopropylmethyl, and the like.

"Lower alkylene" means the divalent linear or branched saturated hydrocarbon radical, having from one to six carbons inclusive, unless otherwise indicated. Examples of lower alkylene radicals include, but are not limited to, methylene, ethylene, propylene, 2-methyl-propylene, butylene, 2-ethylbutylene, and the like.

"Alkoxy" means the radical —O—R, wherein R is a lower alkyl radical as defined herein. Examples of alkoxy radicals include, but are not limited to, methoxy, ethoxy, isopropoxy, and the like.

"Aryl" means the monovalent aromatic hydrocarbon radical consisting of one individual ring, or one or more fused rings in which at least one ring is aromatic in nature, which can optionally be substituted with one or more, preferably one or two, substituents selected independently from hydroxy, cyano, lower alkyl, lower alkoxy, allcylthio, halogen, haloalkyl, hydroxyalkyl, nitro, alkoxycarbonyl, amino, alkylamino, alkylsulfonyl, arylsulfonyl, alkylarninosulfonyl, arylaminosulfonyl, alkylcarbonylamino, arylcarbonylamino, alkylaminocarbonyl, arylaminocarbonyl, alkylsulfonylamino, or arylsulfonylamino unless otherwise indicated. Alternatively, two adjacent atoms of the aryl ring may be substituted with a methylenedioxy or ethylenedioxy group. Examples of aryl radicals include, but are not limited to, phenyl, naphthyl, biphenyl, 2,3-dihydrobenzo[1,4]dioxin-2-yl,2,3-dihydrobenzo[1,4]dioxin-5-yl,6-methyl-benzo[1,3]dioxol-5-yl, 1,3-benzodioxolyl, indanyl, 2,4-dimethyl-phenyl, 2-cyano-phenyl and the like.

"Arylalkyl" (or "aralkyl") means the radical $R^aR^b$—, wherein $R^a$ is an aryl radical as defined herein, and $R^b$ is a lower alkylene radical as defined herein. Examples of arylalkyl radicals include, but are not limited to, benzyl, phenylethyl, 3-phenylpropyl, and the like.

"Cycloalkyl" means the monovalent saturated carbocyclic radical consisting of one or more rings, which can optionally be substituted with one or more, preferably one or two substituents selected independently from hydroxy, cyano, lower alkyl, lower alkoxy, alkylthio, halogen, haloalkyl, hydroxyalkyl, nitro, alkoxycarbonyl, amino, alkylamino, alkylsulfonyl, arylsulfonyl, alkylaminosulfonyl, arylaminosulfonyl, alkylcarbonylamino, alrylcarbonylamino, alkylaminocarbonyl, arylaminocarbonyl, alkylsulfonylamino, or arylsulfonylamino, unless otherwise indicated. Examples of cycloalkyl radicals include, but are not limited to, cyclopropyl, cyclobutyl, 3-ethylcyclobutyl, cyclopentyl, cycloheptyl, and the like.

"Cycloalkylalkyl" means the radical $R^aR^b$—, wherein $R^a$ is a cycloalkyl radical as defined herein, and $R^b$ is an lower alkylene radical as defined herein. Examples of cycloalkylalkyl radicals include, but are not limited to, cyclopropylmethyl, cyclobutylmethyl, cyclohexylmethyl, cyclopentylethyl, and the like.

"Heteroaryl" means the monovalent aromatic cyclic radical having one or more rings, preferably one to three rings, of four to eight atoms per ring, incorporating one, two, or three heteroatoms within the ring (chosen from nitrogen, oxygen, or sulfur) which can optionally be substituted with one or more, preferably one or two substituents selected independently from hydroxy, cyano, lower alkyl, lower alkoxy, alkylthio, halogen, halogenalkyl, hydroxyalkyl, nitro, alkoxycarbonyl, amino, alkylamino, alkylsulfonyl, arylsulfonyl, alkylaminosulfonyl, arylaminosulfonyl, alkylcarbonylamino, alrylcarbonylamino, alkylaminocarbonyl, arylaminocarbonyl, alkylsulfonylamino, or arylsulfonylamino, unless otherwise indicated. Examples of heteroaryl radicals include, but are not limited to, imidazolyl, oxazolyl, thiazolyl, pyrazinyl, thienyl, furanyl, pyridinyl, pyrimidinyl, pyridinazyl, pyrrolyl, quinolinyl, isoquinolinyl, benzofuryl, indazolyl, indolyl, isoindolyl, quinolinyl, isoquinolinyl, naphthyridinyl, and the like.

"Heteroarylalkyl" (or "heteroaralkyl") means the radical of the formula $R^aR^b$—, wherein $R^a$ is a heteroaryl radical as defined herein, and $R^b$ is a lower alkylene radical as defined herein. Examples of heteroarylalkyl radicals include, but are not limited to, 2-pyridinylmethyl, 3-furanylethyl, 2-thienylalkyl, and the like.

"Heterocyclyl" means the monovalent saturated cyclic radical, consisting of one or more rings, preferably one to two rings, of three to eight atoms per ring; incorporating one, two, or three ring heteroatoms (chosen from N, O or $S(O)_{0-2}$), which can optionally be substituted with one or more, preferably one or two substituents selected independently from hydroxy, oxo, cyano, lower alkyl, lower alkoxy, alkylthio, halogen, halogenalkyl, hydroxyalkyl, nitro, alkoxycarbonyl, amino, alkylamino, alkylsulfonyl, arylsulfonyl, alkylaminosulfonyl, arylaminosulfonyl, alkylcarbonylamino, arylcarbonylamino, alkylaminocarbonyl, arylaminocarbonyl, alkylsulfonylamino, or arylsulfonylamino, unless otherwise indicated. Examples of heterocyclyl radicals include, but are not limited to, morpholinyl, piperazinyl, piperidinyl, pyrrolidinyl, tetrahydropyranyl, thiomorpholinyl, and the like.

"Heterocycloalkyl" (or "heterocyclylalkyl") means the radical of the formula $R^aR^b$, wherein $R^a$ is a heterocyclic radical as defined herein, and $R^b$ is a lower alkylene radical as defined herein. Examples of heterocycloalkyl radicals include, but are not limited to, 1-piperazinylmethyl, 2-morpholinomethyl, and the like.

"Halogen", "halo", or "halide" means the radical fluoro, bromo, chloro, and/or iodo.

"Halogenalkyl" or "haloalkyl" means the lower alkyl radical as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Hydroxyalkyl" means the lower alkyl radical as defined herein, substituted with one or more hydroxy groups. Examples of hydroxyalkyl radicals include, but are not limited to, hydroxymethyl, 2-hydroxyethyl, 2-hydroxypropyl, 3-hydroxypropyl, 2-hydroxybutyl, 3-hydroxybutyl, 4-hydroxybutyl, 2,3-dihydroxypropyl, 1,3-dihydroxy-2-propyl, 2,3-dihydroxybutyl, 3,4-dihydroxybutyl, and 2-(hydroxymethyl)-3-hydroxypropyl, and the like.

"Alkylamino" means the radical —$NR^aR^{b'''}$, wherein $R^a$ is a lower alkyl radical as defined herein, and $R^b$ is hydrogen or lower alkyl as defined herein. Examples of alkylamino radicals include, but are not limited to, methylamino, (1-methylpropyl)amino, dimethylamino, methylethylamino, diethylamino, N,N-hydroxyethyl-ethylamino, N,N-methoxyethyl-ethylamino and the like.

"Acyloxy" means the radical RC(O)O—, wherein R is a lower alkyl radical as defined herein. Examples of acyloxy radicals include, but are not limited to, acetoxy, propionyloxy, and the like.

"Alkylcarbonyl" means the radical RC(O)—, wherein R is an optionally substituted lower alkyl radical as defined herein. Examples of alkylcarbonyl radicals include, but are not limited to, formyl, acetyl, propionyl, n-butyryl, sec-butyryl, t-butyryl, iso-propionyl and the like.

"Alkoxycarbonyl" or "alkyl ester" means the radical —C(O)—O—R, wherein R is a lower alkyl radical as defined herein. Examples of alkoxycarbonyl radicals include, but are not limited to, methoxycarbonyl, ethoxycarbonyl, sec-butoxycarbonyl, isopropyloxycarbonyl, and the like.

"Aminocarbonyl" means the radical —C(O)NR$^a$R$^b$, wherein R$^a$ and R$^b$ are independently from each other hydrogen or lower alkyl as defined herein. Examples of alkylaminocarbonyl include, but are not limited to methylaminocarbonyl, dimethylaminocarbonyl, t-butylaminocarbonyl, n-butylaminocarbonyl, isopropylaminocarbonyl and the like.

"Alkoxycarbonylamino" means the radical —NC(O)OR, wherein R is lower alkyl as defined herein. Examples of alkoxycarbonylamino include, but are not limited to t-butyloxycarbonylamino, methoxycarbonylamino and the like.

"Optionally substituted" means that a group may or may not be substituted with one or more, preferably one or two substitutents independently selected from the specified group. For example phenyl optionally substituted with lower alkyl, alkoxy, halogen or cyano means that the phenyl group may or may not be substituted at any position with one or more, preferably one or two substituents independently selected from the group lower alkyl, alkoxy, halogen or cyano.

"Leaving group" means the group with the meaning conventionally associated with it in synthetic organic chemistry, i.e., an atom or group displaceable by a nucleophile. Examples of leaving groups include, but are not limited to, halogen, alkyl- or arylsulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Examples of protecting groups can be found in T. W. Greene et al., *Protective Groups in Organic Chemistry*, (J. Wiley, 2$^{nd}$ ed. 1991) and Harrison et al., *Compendium of Synthetic Organic Methods*, Vol. 1–8 (J. Wiley and Sons 1971–1996).

"Amino-protecting group" means the protecting group that refers to those organic groups intended to protect the nitrogen atom against undesirable reactions during synthetic procedures and includes, but is not limited to, benzyl, benzyloxycarbonyl (carbobenzyloxy, CBZ), p-methoxybenzyloxycarbonyl, p-nitrobenzyloxycarbonyl, tert-butoxycarbonyl (BOC), trifluoroacetyl, and the like. It is preferred to use either BOC or CBZ as the amino-protecting group because of the relative ease of removal, for example by mild acids in the case of BOC, e.g., trifluoroacetic acid or hydrochloric acid in ethyl acetate; or by catalytic hydrogenation in the case of CBZ.

"Deprotection" or "deprotecting" means the process by which a protective group is removed after the selective reaction is completed. Certain protective groups may be preferred over others due to their convenience or relative ease of removal.

"Inert organic solvent" or "inert solvent" means the solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

"Chiral compound" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When chiral centers are present, the stereoisomers may be characterized by the absolute configuration (R or S ) of the chiral centers. Absolute configuration refers to the arrangement in space of the substituents attached to a chiral center. The substituents attached to a chiral center under consideration are ranked in accordance with the Sequence Rule of Cahn, Ingold and Prelog. (Cahn et al. *Angew. Chem. Inter.* Edit. 1966, 5, 385; errata 511; Cahn et al. *Angew. Chem.* 1966, 78, 413; Cahn and Ingold *J. Chem. Soc.* (London) 1951, 612; Cahn et al. *Experientia,* 1956, 12, 81; Cahn et al.,*J. Chem. Educ.*, 1964, 41, 116).

"Atropic isomers" means the isomers owing their existence to restricted rotation caused by hindrance of rotation of large groups about a central bond.

"Substantially pure" means at least about 80 mole percent, more preferably at least about 90 mole percent, and most preferably at least about 95 mole percent of the desired enantiomer or stereoisomer is present compared to other possible configurations.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Acceptable salt" of a compound means salt that possesses the desired pharmacological activity of the parent compound. Such salts include:

(1) an acid addition salt formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalenesulfonic acid, propionic acid, salicylic acid, succinic acid, dibenzoyl-L-tartaric acid, tartaric acid, p-toluene sulfonic acid, trimethylacetic acid, 2,2,2-trifluoroacetic acid, and the like; or (2) a salt formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate and sodium hydroxide.

The preferred acceptable salts are the salts formed from hydrochloric acid, and 2,2,2-trifluoroacetic acid. It should be understood that all references to acceptable salt include solvent addition forms (solvates) or crystal forms (polymorphs) as defined herein, of the same acid addition salt.

"Crystal forms" (or polymorphs) means crystal structures in which a compound can crystallize in different crystal packing arrangements, all of which have the same elemental composition. Different crystal forms usually have different X-ray diffraction patterns, infrared spectra, melting points, density, hardness, crystal shape, optical and electrical properties, stability and solubility. Recrystallization solvent, rate of crystallization, storage temperature, and other factors may cause one crystal form to dominate.

"Solvate" means solvent addition form that contains either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate.

"Prodrug" means a pharmacologically inactive form of a compound which is metabolized in vivo, e.g., by biological fluids or enzymes, by a subject after administration into a pharmacologically active form of the compound in order to produce the desired pharmacological effect. The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action*, by Richard B. Silverman, Academic Press, San Diego, 1992. Chapter 8: "Prodrugs and Drug delivery Systems" pp.352–401; *Design of Prodrugs*, edited by H. Bundgaard, Elsevier Science, Amsterdam, 1985; *Design of Biopharmaceutical Properties through Prodrugs and Analogs*, edited. by E. B. Roche, American Pharmaceutical Association, Washington, 1977; and *Drug Delivery Systems*, edited by R. L. Juliano, Oxford Univ. Press, Oxford, 1980.

"Subject" means mammals and non-mammals. Mammals means any member of the mammalian class including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, reptiles and the like.

"Therapeutically effective amount" means an amount of a compound that, when administered to a subject for treating a disease state, is sufficient to effect such treatment for the disease state. The "therapeutically effective amount" will vary depending on the compound, and disease state being treated, the severity or the disease treated, the age and relative health of the subject, the route and form of administration, the judgement of the attending medical or veterinary practitioner, and other factors.

"Pharmacological effect" as used herein encompasses effects produced in the subject that achieve the intended purpose of a therapy. In one preferred embodiment, a pharmacological effect means that primary indications of the subject being treated are prevented, alleviated, or reduced. For example, a pharmacological effect would be one that results in the prevention, alleviation or reduction of primary indications in a treated subject. In another preferred embodiment, a pharmacological effect means that disorders or symptoms of the primary indications of the subject being treated are prevented, alleviated, or reduced. For example, a pharmacological effect would be one that results in the prevention or reduction of primary indications in a treated subject.

"Disease state" means any disease, condition, symptom, or indication.

"Treating" or "treatment" of a disease state includes:

(1) preventing the disease state, i.e. causing the clinical symptoms of the disease state not to develop in a subject that may be exposed to or predisposed to the disease state, but does not yet experience or display symptoms of the disease state.

(2) inhibiting the disease state, i.e., arresting the development of the disease state or its clinical symptoms, or (3) relieving the disease state, i.e., causing temporary or permanent regression of the disease state or its clinical symptoms.

"Specific alpha-1 adrenergic receptor" as used herein, refers to a distinct member of the group or class of adrenoceptors, which may be selected from the human alpha-1A (previously known as alpha-1C), alpha-1B, alpha-1D, and alpha-1L adrenergic receptors. Preferred species from which may be derived or isolated alpha1-adrenergic receptor subtype polypeptides, genes encoding and alpha-1 adrenergic receptor subtype, and/or cells, tissues and organs that express one or more alpha-1 adrenergic receptor subtype, include human, bovine, rat, murine, porcine, and the like. A more preferred species is human.

"Alpha-1B adrenergic receptor" or "alpha-1B adrenoceptor" means the specific alpha1-adrenoceptor expressed in numerous tissues, most notably in the liver, heart, and cerebral cortex. Alpha-1B adrenoceptors are also present in areas of the spinal cord, which receive input from sympathetic neurons originating in the pontine micturition center.

"Antagonist" means a molecule, such as a compound, a drug, an enzyme inhibitor, or a hormone, that diminishes or prevents the action of another molecule or receptor site.

"Trauma" means any wound or injury. Trauma can produce, for example, acute and/or chronic pain, inflammatory pain, and neuropathic pain.

"Pain" means the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (*Dorland's Illustrated Medical Dictionary*, 28$^{th}$ Edition, W. B. Saunders Company, Philadelphia, Pa.). The goal of treatment of pain is to reduce the degree of severity of pain perceived by a treatment subject.

"Disorders of the urinary tract" or "uropathy" used interchangeably with "symptoms of the urinary tract" means the pathologic changes in the urinary tract. Examples of urinary tract disorders include, but are not limited to, incontinence, benign prostatic hypertrophy (BPH), prostatitis, detrusor hyperreflexia, outlet obstruction, urinary frequency, nocturia, urinary urgency, overactive bladder, pelvic hypersensitivity, urge incontinence, urethritis, prostatodynia, cystitis, idiophatic bladder hypersensitivity, and the like.

"Overactive bladder" or "detrusor hyperactivity" includes, but is not limited to, the changes symptomatically manifested as urgency, frequency, altered bladder capacity, incontinence, micturition threshold, unstable bladder contractions, sphincteric spasticity, detrusor hyperreflexia (neurogenic bladder), detrusor instability, and the like.

"Outlet obstruction" includes, but is not limited to, benign prostatic hypertrophy (BPH), urethral stricture disease, tumors, low flow rates, difficulty in initiating urination, urgency, suprapubic pain, and the like.

"Outlet insufficiency" includes, but is not limited to, urethral hypermobility, intrinsic sphincteric deficiency, mixed incontinence, stress incontinence, and the like.

"Pelvic Hypersensitivity" includes, but is not limited to, pelvic pain, interstitial (cell) cystitis, prostadynia, prostatis, vulvadynia, urethritis, orchidalgia, overactive bladder, and the like.

"Disease states associated with the Central Nervous System (CNS)" or "CNS disease states" mean neurological and/or psychiatric changes in the CNS, e.g., brain and spinal cord, which manifest in a variety of symptoms. Examples of CNS disease states include, but are not limited to, cerebrovascular deficiency; psychoses including paranoia and schizophrenia; attention deficiency and autism; bipolar disorder; anxiety disorders including anticipatory anxiety (e.g., prior to surgery, dental work and the like); obsessive/compulsive disorders; posttraumatic stress disorders; eating disorders including anorexia and bulimia; sleep disorders; convulsive disorders including epilepsy and withdrawal from addictive substances; cognitive diseases including Parkinson's disease and dementia; depression; mania; seasonal affective disorder (SAD); convulsions and anxiety caused by withdrawal from addictive substances such as opiates, benzodiazepines, nicotine, alcohol, cocaine, and other substances of abuse; and improper thermoregulation.

Nomenclature

The naming and numbering of the compounds of this invention is illustrated below:

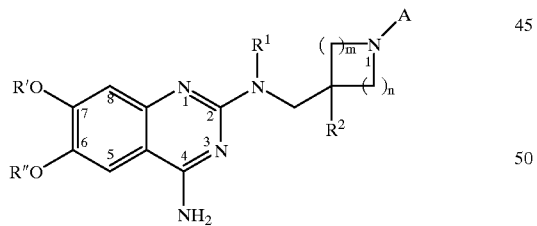

In general, the nomenclature used in this Application is based on Autonom™ v. 4.0, a Beilstein Institute computerized system for the generation of IUPAC systematic nomenclature.

For example, a compound of Formula (I) wherein $R^1$ is —$CH_3$, $R^2$ is phenyl, m is 2, n is 2, and A is —$COR^3$, wherein $R^3$ is —$(CH_2)_3OH$ is named:

1-(4-{[(4-amino-6,7-dimethoxy-quinazolin-2-yl)-methyl-amino]-methyl}-4-phenyl-piperidin-1-yl)-4-hydroxy-butan-1-one.

Similarly, a compound of Formula (I) wherein $R^1$ is —$CH_3$, $R^2$ is phenyl, m is 2, n is 2, and A is —$COR^3$, wherein $R^3$ is furanyl is named:

1-{4-[(4-amino-6,7-dimethoxy-quinazolin-2-ylamino)-methyl]-4-phenyl-piperidin-1-yl}-1-furan-2yl-methanone A compound of Formula (I) wherein $R^1$ is —$CH_3$, $R^2$ is phenyl, m is 2, n is 2, and A is —$SO_2R^3$, wherein $R^3$ is isopropyl is named:

6,7-dimethoxy-$N^2$-methyl-$N^2$-[1'-(propane-2-sulfonyl)-2',3',5',6'-tetrahydro-1'H-[2,4']bipyridinyl-4'-ylmethyl]-quinazoline-2,4-diamine.

Additionally a compound of Formula (I) wherein $R^1$ is —$CH_3$, $R^2$ is phenyl, m is 2, n is 2, and A is —$CH_2R^3$, wherein $R^3$ is benzyl is named:

1-(4-{[(4-amino-6,7-dimethoxy-quinazolin-2-yl)-methyl-amino]-methyl}-4-phenyl-piperidin-1-yl)-2-phenyl-ethanone.

Preferred Compounds

Among compounds of the present invention set forth in the Summary of the Invention, certain compounds of Formula (I), or acceptable prodrug, salt or solvate thereof, are preferred:

$R^1$ is hydrogen or lower alkyl; preferably, $R^1$ is lower alkyl; and even more preferably, $R^1$ is methyl.

$R^2$ is lower alkyl, aryl, heterocyclyl, heteroaryl or aryl, all optionally substituted with lower alkyl, alkoxy, halogen or cyano; more preferably, $R^2$ is aryl optionally substituted with lower alkyl, alkoxy, halogen or cyano; and even more preferably $R^2$ is phenyl optionally substituted with lower alkyl, alkoxy, halogen or cyano.

R' and R" are each independently lower alkyl; more preferably R' and R" are each independently methyl.

A is preferably hydrogen, —$(CH_2)_{0-1}R^3$, —$C(O)R^3$, $SO_2R^3$, —$C(O)OR^3$, —$C(O)NR^4R^5$, —$SO_2NR^4R^5$, —$C(NR)R^3$ or $C(NR^6)NR^4R^5$; more preferably —$(CH_2)_{0-1}R^3$, —$C(O)R^3$, $SO_2R^3$, —$C(O)NR^4R^5$, —$SO_2NR^4R^5$, —$C(NR^6)R^3$, or —$C(NR^6)NR^4R^5$, and even more preferably, A is —$C(O)R^3$, or —$SO_2R^3$.

$R^3$ is independently in each occurrence lower alkyl, optionally substituted with halogen, amino, alkylamino, hydroxy, alkoxy, acyloxy, aminocarbonyl, alkoxycarbonylamino, nitro, or cyano; aryl; arylalkyl; heteroaryl; heteroarylalkyl; cycloalkyl; cycloalkylalkyl; heterocyclyl; or heterocyclylalkyl; more preferably, $R^3$ is lower alkyl or cycloalkyl optionally substituted with halogen, amino, alkylamino, hydroxy, alkoxy, acyloxy, aminocarbonyl, alkoxycarbonylamino, nitro, or cyano; and even more preferably, $R^3$ is independently in each occurrence lower alkyl optionally substituted with fluoro, hydroxy or alkoxy.

$R^4$ and $R^5$ are each independently from each other hydrogen, or $R^4$ and $R^5$ taken together with the nitrogen to which they are attached form a 5- to 7-membered ring, optionally incorporating one or two additional ring heteroatoms chosen from N, S, or O.

$R^6$ is hydrogen, lower alkyl or cyano.

n is an integer ranging from 0 to 2 inclusive, and m is an integer from 0 to 3 inclusive, on condition that m+n is equal or larger than 2; more preferably n is 2 and m is 2.

Other preferred compounds of the present invention include the acceptable salts of the compounds of the present invention wherein the preferred pharmaceutically acceptable salts are formed from hydrochloric acid; or trifluoroacetic acid.

Exemplary particularly preferred compounds, or acceptable prodrug, salt or solvate thereof, include:

1-(4-{[(4-Amino-6,7-dimethoxy-quinazolin-2-yl)-methylamino ]-methyl}-4-phenyl-piperidin-1-yl)-1-cyclopropyl-methanone;

6,7-Dimethoxy-$N^2$-methyl-$N^2$-[4-phenyl-1-(propane-2-sulfonyl)-piperidin-4-ylmethyl]-quinazoline-2,4-diamine;

1-(4-{[(4-Amino-6,7-dimethoxy-quinazolin-2-yl)-methylamino]-methyl}-4-phenyl-piperidin-1-yl)-4,4,4-trifluoro-butan-1-one;

(S)-1-(4-{[(4-Amino-6,7-dimethoxy-quinazolin-2-yl)-methyl-amino]-methyl}-4-phenyl-piperidin-1-yl)-3-hydroxy-butan-1-one;

(R)-1-(4-{[(4-Amino-6,7-dimethoxy-quinazolin-2-yl)-methyl-amino]-methyl}-4-phenyl-piperidin-1-yl)-3-hydroxy-butan-1-one;

1-(4-{[(4-Amino-6,7-dimethoxy-quinazolin-2-yl)-methylamino]-methyl}-4-phenyl-piperidin-1-yl)-1-(tetrahydro-duran-2yl-methanone;

1-(4-{[(4-Amino-6,7-dimethoxy-quinazolin-2-yl)-methylamino]-methyl}-4-phenyl-piperidin-1-yl)-1-pyrrolidin-2-yl-methanone;

$N^2$-(1-Cyclopropanesulfonyl-4-phenyl-piperidin-4-ylmethyl)-6,7-dimethoxy-$N^2$-methyl-quinazoline-2,4-diamine;

4-{[(4-Amino-6,7-dimethoxy-quinazolin-2-yl)-methylamino]-methyl}-4-phenyl-piperidine-1-sulfonic acid dimethylamide;

1-(4-{[(4-Amino-6,7-dimethoxy-quinazolin-2-yl)-methylamino]-methyl}-4-phenyl-piperidin-1-yl)-butan-1-one;

1-[4-{[(4-Amino-6,7-dimethoxy-quinazolin-2-yl)-methylamino]-methyl}-4-(4-fluoro-phenyl)-piperidin-1yl]-butan-1-one:

1-(4-{[(4-Amino-6,7-dimethoxy-quinazolin-2-yl)-methylamino]-methyl}-4-phenyl-piperidin-1-yl)-1-phenyl-methanone;

4-{[(4-Amino-6,7-dimethoxy-quinazolin-2-yl)-methylamino]-methyl}-4-phenyl-piperidine-1-carboxylic acid pyridin-3-ylamide;

$N^2$-[1-(2-Cyclopropyl-1-imino-ethyl)-4-phenyl-piperidin-4-ylmethyl]-6,7-dimethoxy-$N^2$-methyl-quinazoline-2,4-diamine;

4-{[(4-Amino-6,7-dimethoxy-quinazolin-2-yl)-methylamino]-methyl}-N-methyl-4-phenyl-piperidine-1-carboxamidine; or $N^2$-[1-(2,3-Dihydro-benzo[1,4]dioxin-6-ylmethyl)-4-phenyl-piperidin-4-ylmethyl]-6,7-dimethoxy-$N^2$-methyl-quinazoline-2,4-diamine.

General Synthetic Reaction Schemes

Compounds of the present invention may be made by the methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention may be synthesized, and various modifications to these synthetic reaction schemes may be made and will be suggested to one skilled in the art having referred to the disclosure contained in this Application.

The starting materials and the intermediates of the synthetic reaction schemes may be isolated and purified if desired using conventional techniques including but not limited to filtration, distillation, crystallization, chromatography, and the like. Such materials may be characterized using conventional means, including physical constants and spectral data.

Unless specified to the contrary, the reactions described herein preferably take place at atmospheric pressure over a temperature range from about −20° C. to reflux, and most preferably at about room (or ambient) temperature, e.g., about 20° C.

In general, the compounds of Formula (I) are prepared following the method described in Scheme A.

Scheme A

Scheme A describes a method of preparing a compound of Formula (I) wherein A, $R^1$ and $R^2$ are as described in the Summary of the Invention.

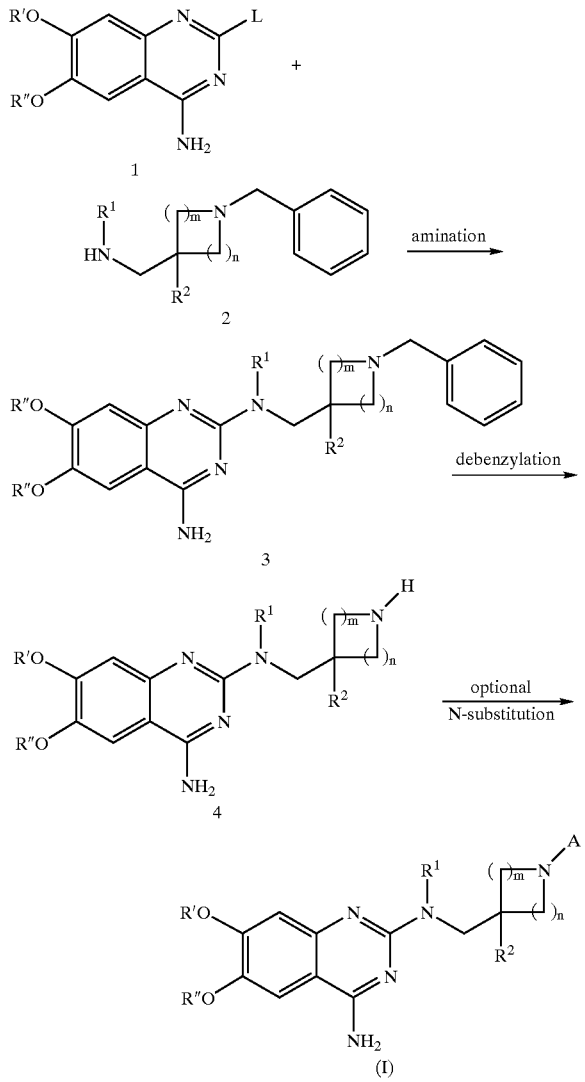

A compound of Formula (I) can be prepared by reacting the free amine group of compound 2 (prepared according to DeGraw et al., *J. Med. Chem.* 1967, 10, 174) with a compound of formula 1 wherein L is a leaving group such as halogen, preferably chloro, optionally in the presence of a base such as sodium carbonate, potassium carbonate, diisopropylethylamine, tributylamine, or triethylamine, in an inert solvent such as lower alkanol, DMSO, or DMF, to obtain a compound 3. The benzyl group of compound 3 can be removed by procedures known to one skilled in the art to yield the free amino base 4. For example, a method of debenzylation can be carried out by hydrogenation. The hydrogenation is carried out with a suitable catalyst (e.g., 10% palladium on carbon (Pd/C), palladium hydroxide, palladium acetate, etc., preferably 10% Pd/C) in the presence of ammonium formate and in an appropriate solvent, typically an alcohol, preferably methanol, preferably at about 20° C. to about 100° C., and more preferably at reflux. Alternatively, the benzyl group can be removed by treating the protected compound with the catalyst under a hydrogen atmosphere at 1 to 50 psi, and preferably at approximately 15 psi, at about 20° C. to about 100° C., and preferably at about 20° C. to about 60° C. Compounds of Formula (I), where A is other than benzyl or hydrogen may be obtained from compound 4. Functionalizing the secondary nitrogen atom with an appropriate reagent by procedures known to one skilled in the art can form amides, ureas, carbamates, sulfonamides, guanidines, sulfamides and amidines of Formula (I).

Exemplary preparations of a compound of Formula (I) are given in Examples 1 to 13.

General Utility

Alpha-1 adrenergic receptors mediate the contractile state of smooth muscle tissue and are present in the human prostate, bladder neck and urethra. Sympathetic activity produces contraction of vascular smooth muscle which leads to elevated blood pressures. Alpha-1 adrenergic receptor stimulation also produces glycogenolysis, growth and hypertrophy of cardiac myocytes and contraction of urethral and bladder neck smooth muscle, leading to increased resistance in urinary outflow. Thus, alpha-1 adrenoceptor antagonists may be useful in treating disorders or symptoms related to uropathies such as obstruction due to benign prostatic hyperplasia (BPH). (See U.S. Pat. No. 5,859,014; Lepor, H., *The Prostate Supplement*, 1990, 3, 75–84 and International Publication No. WO 95/25726.)

Experimental evidence supports a therapeutic role for alpha-1 adrenergic receptor antagonists in treating prostatic hyperplasia. (See for example, Lepor, H., *The Prostate Supplement* 1990, 3, 75–84.) Obstruction of the urinary tract can occur as a result of prostatic hyperplasia and excessive prostatic constriction of the urethra. This in turn leads to diminished urinary flow rates and an increased urgency and frequency of urination.

In a preferred embodiment, the compounds of this invention are useful for treating disease states which can be ameliorated by modulation, preferably by blockade of alpha-1 adrenoceptors, such as reduction or alleviation of urinary tract disorders, for example, pelvic hypersensitivity (including interstitial cystitis, prostatitis, pelvic pain syndrome, infectious cystitis, prostatodynia, and the like), overactive bladder, urinary frequency, nocturia, urinary urgency, detrusor hyperreflexia, outlet obstruction, prostatitis, urge incontinence, urethritis, idiophatic bladder hypersensitivity, and the like. Compounds of this invention may also be useful for treating male erectile dysfunction and female sexual dysfunction.

In a more preferred embodiment, the compounds of this invention are useful for treating disease states which can be ameliorated by blockade of alpha-1B adrenoceptors. Alpha-1B adrenoceptors are present in the liver, heart and cerebral cortex and are believed to be involved in mediating vascular contractile and blood pressure responses. Additionally, alpha-1B adrenoceptors are also present in areas of the spinal cord which receive input from sympathetic neurons originating in the pontine micturition center and are presumed to be involved in the regulation of bladder function. Selective blockade of the alpha-1B adrenoceptor may lead to the symptomatic treatment of pelvic hypersensitivity (including interstitial cystitis, prostatitis, pelvic pain syndrome, infectious cystitis, prostatodynia, and the like), urethritis, overactive bladder (manifested as urge incontinence), detrusor hyperreflexia, outlet obstruction (resulting from benign prostatic hypertrophy and prostatitis), and other conditions of idiopathic bladder hypersensitivity.

Additionally, alpha -1B adrenoceptor antagonists are useful as analgesic/antihyperalgesic therapies for treating pain, including symptoms of acute pain, inflammatory pain, neuropathic pain (including thermal and mechanical hyperalgesia as well as thermal and mechanical allodynia), complex regional pain syndromes (including reflex sympathetic dystrophy, causalgia and sympathetically maintained pain). (See, commonly owned U.S. patent application Ser. No. 09/521,185 by Ford et al. entitled "*A Method For Screening Compounds For* Alpha-1B *Adrenergic Receptor Antagonist and Analgesic Activity*," filed on Mar. 17, 1999, the disclosure of which is hereby incorporated by reference in its entirety).

Additionally, alpha-1B adrenoceptor antagonists are useful for the treatment of CNS disorders including, but not limited to, general anxiety disorder, panic disorder, sleep disorders, posttraumatic stress disorder, and schizophrenia.

These and other therapeutic uses are described, for example, in *Goodman & Gilman's, The Pharmacological Basis of Therapeutics*, ninth edition, McGraw-Hill, New York, 1996, Chapter 26:601–616; and Coleman, R. A., *Pharmacological Reviews* 1994, 46:205–229.

Testing

The pharmacology of the compounds of this invention was determined by art recognized procedures. The in vitro techniques for determining the affinities of test compounds at alpha-1 adrenoceptor subtypes in radioligand binding and functional assays are described in Example 21.

The effect of the compounds of this invention on blood pressure can be evaluated by any method known in the art. Examples of such methods are the Rat In Vivo Blood Pressure Assay, the Rat in Vivo Tilt-Response Assay, and the Dog In Vivo Blood and Intraurethral Pressure assay. An in vivo assay for measuring the blood pressure lowering effects of test compounds in normotensive rats is described in Example 22.

The analgesic activity of the compounds of this invention can be evaluated by any method known in the art. Examples of such methods are the Tail-flick test (D'Amour et al. *J. Pharmacol Exp. and Ther.* 1941, 72, 74–79), the Rat Tail Immersion Model, the Carrageenan-induced Paw Hyperalgesia Model, the Formalin Behavioral Response Model (Dubuisson et al., *Pain* 1977, 4, 161–174), the Von Frey Filament Test (Kim et al., *Pain,* 1992, 50, 355–363), the Chronic Constriction Injury, the Radian Heat Model, and the Cold Allodynia Model (Gogas et al., *Analgesia,* 1997, 3:111–118). An in vivo assay for measuring the effect of test compounds on the pain response to radiant heat in neuropathic rats is described in Example 23.

The potential of alpha-1 adrenoceptor antagonists to cause postural hypotension can be evaluated for example with the blood withdrawal model in conscious rat. An in vivo assay for measuring the effect of test compounds on postural hypotension in conscious rats is described in Example 24.

Preferred compounds of this invention generally demonstrate selectivity for the alpha 1B-subtype over the alpha-1A and alpha-1D subtype. The compounds of this invention may reduce both obstructive and irritative symptoms in patients with BPH. Additionally they may be useful in the treatment of pain or in the treatment of CNS disorders. The reduction of alpha-1A and alpha-1D adrenoceptor antagonism is expected to lead to reduced or fewer side effects than those associated with the use of non-subtype-selective agents.

Administration and Pharmaceutical Composition

The present invention includes pharmaceutical compositions comprising at least one compound of the present invention, or acceptable prodrug, salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or acceptable salt thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoro-methane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 14–20.

EXAMPLES

The following preparations and examples are given to enable those skilled in the art to more clearly understand and to practice the present invention. They should not be considered as limiting the scope of the invention, but merely as being illustrative and representative thereof.

Example 1

$N^2$-(1-Benzyl-4-phenyl-piperidin-4-ylmethyl)-6,7-dimethoxy-$N^2$-methyl-quinazoline-2,4-diamine 10

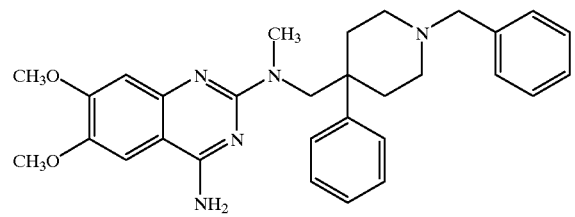

A mixture of 2-chloro-6,7-dimethyl-quinazolin-4-ylamine 1 (X=Cl) (900 mg), (1-benzyl-4-phenyl-piperidin-4-ylmethyl)-methyl-amine 2a ($R^1$=$CH_3$ and $R^2$=phenyl) (440 mg) and potassium carbonate (250 mg) in 1-butanol (20 ml) was refluxed for 18 hours. The cooled reaction mixture was filtered, the filtrate was evaporated, and the residue was distributed between water and dichloromethane. The organic phase was dried over potassium carbonate, filtered, and evaporated. The residue was purified by flash chromatography on silica gel to provide 1.3 g of $N^2$-(1-Benzyl-4-phenyl-piperidin-4-ylmethyl)-6,7-dimethoxy-$N^2$-methyl-quinazoline-2,4-diamine 10, as an oil, MS: 485 ($M^+$).

Similarly, following the procedure as described above, but replacing (1-benzyl-4-phenyl-piperidin-4-ylmethyl)-methyl-amine 2a with other appropriate compounds of general Formula 2, and utilizing the modifications known to those skilled in the art, the additional compounds of the general Formula (I) wherein A is benzyl were prepared:

N²-(1-Benzyl-4-morpholin-4-yl-piperidin-4-ylmethyl)-6,7-dimethoxy-N²-methyl-quinazoline-2,4-diamine 23, MS: 507 ([M+H]⁺);

N²-(1'-Benzyl-[1,4']bipiperidinyl-4'-ylmethyl)-6,7-dimethoxy-N²-methyl-quinazoline-2,4-diamine 24, MS 504 ([M+H]⁺);

N²-(1-Benzyl-4-phenyl-piperidin-4-ylmethyl-6,7-dimethoxy-quinazoine-2,4-diamine 25, MS: 483 (M⁺);

N²-[1-Benzyl-4-(2-methoxy-phenyl)-piperidin-4-ylmethyl]-6,7-dimethoxy-N²-methyl-quinazoline-2,4-diamine 26, MS: 527 (M⁺);

N²-(1'-Benzyl-2',3',5',6'-tetrahydro-1H-[3,4']bipyridinyl-4'-ylmethyl)-6,7 -dimethoxy-N²-methyl-quinazoline-2,4-diamine 27, MS:499 ([M+H]⁺);

N²-[1-Benzyl-4-(4-fluoro-phenyl)-piperidin-4-ylmethyl]-6,7-dimethoxy-N²-methyl-quinazoline-2,4-diamine 28, MS: 516 ([M+H]⁺);

N²-[1-Benzyl-4-(4-methoxy-phenyl)-piperidin-4-ylmethyl]-6,7-dimethoxy-N²-methyl-quinazoline-2,4-diamine 29, MS: 528 ([M+H]⁺);

N²-(1'-Benzyl-2',3',5',6'-tetrahydro-1H-[2,4']bipyridinyl-4'-ylmethyl)-6,7 -dimethoxy-N²-methyl-quinazoline-2,4-diamine 30, MS: 499 ([M+H]⁺);

N²-(1-Benzyl-4-methyl-piperidin-4-ylmethyl)-6,7-dimethoxy-N²-methyl-quinazoline-2,4-diamine 31, MS:436([M+H]⁺); or N²-(1-Benzyl-4-thiophen-2-yl-piperidin-4-ylmethyl)-6,7-dimethoxy-N²-methyl-quinazoline-2,4-diamine 32, MS: 504 ([M+H]⁺).

Example 2

6,7-Dimethoxy-N²-(4-phenyl-piperidin-4-ylmethyl)-N²-methyl-quinazoline-2,4-diamine 11

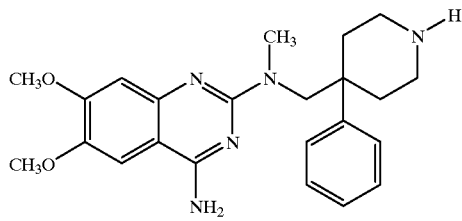

To a solution of N²-(1-Benzyl-4-phenyl-piperidin-4-ylmethyl)-6,7-dimethoxy-N²-methyl-quinazoline-2,4-diamine 10, (1.3 g) and ammonium formate (2.2 g) in 24 ml methanol and 6 ml water was added 10% Pd-C (250 mg). After stirring under reflux for two hours, the reaction mixture was cooled and filtered through celite®. The filtrate was concentrated to a small volume, made basic with potassium carbonate, and extracted with dichloromethane. The extract was dried over potassium carbonate, filtered, and evaporated. The residue was chromatographed on silica gel to provide 800 mg of 6,7-dimethoxy-N²-(4-phenyl-piperidin-4-ylmethyl)-N²-methyl-quinazoline-2,4-diamine 11 as a white powder, MS: 407 (M⁺).

Similarly, following the procedure described in Example 2, but replacing N²-(1-Benzyl-4-phenyl-piperidin-4-ylmethyl)-6,7-dimethoxy-N²-methyl-quinazoline-2,4-diamine 10 with other appropriate compounds of general Formula 3, and utilizing the modifications known to those skilled in the art, the additional compounds of the general Formula (I) wherein A is hydrogen were prepared:

6,7-Dimethoxy-N²-(4-phenyl-piperidin-4-ylmethyl)-quinazoline-2,4-diamine 33, MS: 393 (M⁺);

N²-[1,4']Bipiperidinyl-4'-ylmethyl-6,7-dimethoxy-N²-methyl-quinazoline-2,4-diamine 34, MS: 415 (M⁺);

6,7-Dimethoxy-N²-[4-(2-methoxy-phenyl)-piperidin-4-ylmethyl]-N²-methyl-quinazoline-2, 4-diamine 35, MS: 437 (M⁺);

6,7-Dimethoxy-N²-methyl-N²-(4-morpholin-4-yl-piperidin-4-ylmethyl)-quinazoline-2,4-diamine 36, MS: 417 ([M+H]⁺);

6,7-Dimethoxy-N²-methyl-N²-(2',3',5',6'-tetrahydro-1H-[3,4']bipyridinyl-4'-ylmethyl)-quinazoline-2,4-diamine 37, MS: 409 ([M+H]⁺);

N²-[4-(4-Fluoro-phenyl)-piperidin-4-ylmethyl]-6,7-dimethoxy-N²-methyl-quinazoline-2,4-diamine 38, MS: 426 ([M+H]⁺);

6,7-Dimethoxy-N²-[4-(4-methoxy-phenyl)-piperidin-4-ylmethyl]-N²-methyl-quinazoline-2,4-diamine 39, MS: 438 ([M+H]⁺);

6,7-Dimethoxy-N²-methyl-N²-(2',3',5',6'-tetrahydro-1H-[2,4']bipyridinyl-4'-ylmethyl)-quinazoline-2,4-diamine 40, MS: 409 ([M+H]⁺);

6,7-Dimethoxy-N²-methyl-N²-(4-thiophen-2-yl-piperidin-4-ylmethyl)-quinazoline-2,4-diamine 41, MS: 414 ([M+H]⁺); or 6,7-Dimethoxy-N²-methyl-N²-(4-methyl-piperidin-4-ylmethyl)-quinazoline-2,4-diamine 42, MS: 346 ([M+H]⁺).

Example 3

1-(4-{[(4-Amino-6,7-dimethoxy-quinazolin-2-yl)-methyl-amino]-methyl}-4-phenyl-piperidin-1-yl)-1-cyclopropyl-methanone 12

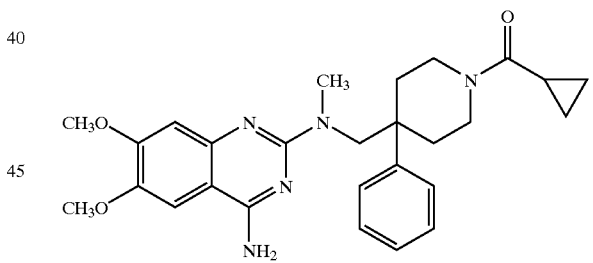

A mixture of 6,7-dimethoxy-N²-(4-phenyl-piperidin-4-ylmethyl)-N²-methyl-quinazoline-2,4-diamine 11 (125 mg), ethyl acetate (10 ml) and aq. sodium bicarbonate (10 ml) was stirred vigorously while 40 μL of cyclopropylcarbonyl chloride were added slowly via syringe. After 30 min., the reaction mixture was worked up as usual to yield 1-(4-{[(4-Amino-6,7-dimethoxy-quinazolin-2-yl)-methyl-amino]-methyl}-4-phenyl-piperidin-1-yl)-1-cyclopropyl-methanone 12, MS: 476 ([M+H]⁺) The crude base was converted to the hydrochloride salt as a white powder (120 mg).

Similarly, following the procedure described in Example 3, but replacing cyclopropylcarbonyl chloride with other appropriate carbonyl chlorides, optionally replacing 6,7-dimethoxy-N²-(4-phenyl-piperidin-4-ylmethyl)-N²-methyl-quinazoline-2,4-diamine 11 with quinazolines from Example 2, and utilizing the modifications known to those skilled in the art, the additional compounds of the general Formula (I) wherein A is —C(O)R³ were prepared:

1-(4-{[(4-Amino-6,7-dimethoxy-quinazolin-2-yl)-methyl-amino]-methyl}-4-phenyl-piperidin-1-yl)-1-furan-2-yl-methanone 43, MS: 501 (M⁺);

1-{4-[(4-Amino-6,7-dimethoxy-quinazolin-2-ylamino)-methyl]-4-phenyl-piperidin-1-yl}-1-furan-2-yl methanone 44, MS: 488 ([M+H]⁺);

1-(4'-{[(4-Amino-6,7-dimethoxy-quinazolin-2-yl)-methyl-amino]-methyl}-[1,4']bipiperidinyl-1'-yl)-1-furan-2-yl-methanone 45, MS: 508 (M⁺);

1-(4-{[(4-Amino-6,7-dimethoxy-quinazolin-2-yl)-methyl-amino]-methyl}-4-morpholin-4-yl-piperidin-1-yl)-1-furan-2-yl-methanone 46, MS: 511 ([M+H]⁺);

1-(4-{[(4-Amino-6,7-dimethoxy-quinazolin-2-yl)-methyl-amino]-methyl}-4-phenyl-piperidin-1-yl)-2-phenyl-ethanone 47, MS: 526 ([M+H]⁺);

1-(4-{[(4-Amino-6,7-dimethoxy-quinazolin-2-yl)-methyl-amino]-methyl}-4-phenyl-piperidin-1-yl)-butan-1-one 48, MS: 478 ([M+H]⁺);

1-(4-{[(4-Amino-6,7-dimethoxy-quinazolin-2-yl)-methyl-amino]-methyl}-4-phenyl-piperidin-1-yl)-ethanone 49, MS: 450 ([M+H]⁺);

1-(4-{[(4-Amino-6,7-dimethoxy-quinazolin-2-yl)-methyl-amino]-methyl}-4-phenyl-piperidin-1-yl)-propan-1-one 50, MS: 464 ([M+H]⁺);

1-(4-{[(4-Amino-6,7-dimethoxy-quinazolin-2-yl)-methyl-amino]-methyl}-4-phenyl-piperidin-1-yl)-2-methyl-propan-1-one 51, MS: 478 ([M+H]⁺);

1-(4-{[(4-Amino-6,7-dimethoxy-quinazolin-2-yl)-methyl-amino]-methyl}-4-phenyl-piperidin-1-yl)-2,2-dimethyl-propan-1-one 52, MS: 492 ([M+H]⁺);

1-(4-{[(4-Amino-6,7-dimethoxy-quinazolin-2-yl)-methyl-amino]-methyl}-4-phenyl-piperidin-1-yl)-1-pyridin-3-yl-methanone 53, MS: 513 ([M+H]⁺);

1-(4-{[(4-Amino-6,7-dimethoxy-quinazolin-2-yl)-methyl-amino]-methyl}-4-phenyl-piperidin-1-yl)-1-(4-methoxy-phenyl)-methanone 54, MS: 542 ([M+H]⁺);

4-{[(4-Amino-6,7-dimethoxy-quinazolin-2-yl)-methyl-amino]-methyl}-4-phenyl-piperidine-1-carboxylic acid diethylamide 55, MS: 507 ([M+H]⁺);

1-(4-{[(4-Amino-6,7-dimethoxy-quinazolin-2-yl)-methyl-amino]-methyl}-4-phenyl-piperidin-1-yl)-1-phenyl-methanone 56, MS: 512 ([M+H]⁺);

1-(4-{[(4-Amino-6,7-dimethoxy-quinazolin-2-yl)-methyl-amino]-methyl}-4-phenyl-piperidin-1-yl)-1-(4-chloro-phenyl)-methanone 57, MS: 546 ([M+H]⁺);

1-(4-{[(4-Amino-6,7-dimethoxy-quinazolin-2-yl)-methyl-amino]-methyl}-4-phenyl-piperidin-1-yl)-1-thiophen-2-yl-methanone 58, MS: 518 ([M+H]⁺);

1-[4-{[(4-Amino-6,7-dimethoxy-quinazolin-2-yl)-methyl-amino]-methyl}-4-(4-fluoro-phenyl)-piperidin-1-yl]-butan-1-one 59, MS: 496 ([M+H]⁺);

1-(4-{[(4-Amino-6,7-dimethoxy-quinazolin-2-yl)-methyl-amino]-methyl}-4-methyl-piperidin-1-yl)-butan-1-one 60, MS: 416 ([M+H]⁺);

1-(4'-{[(4-Amino-6,7-dimethoxy-quinazolin-2-yl)-methyl-amino]-methyl}-3',4',5',6'-tetrahydro-2'H-[2,4']bipyridinyl-1'-yl)-propan-1-one 61, MS: 464 (M⁺);

1-(4'-{[(4-Amino-6,7-dimethoxy-quinazolin-2-yl)-methyl-amino]-methyl}-3',4',5',6'-tetrahydro-2'H-[2,4']bipyridinyl-1'-yl)-1-furan-2-yl-methanone 62, MS: 502 (M⁺);

1-(4'-{[(4-Amino-6,7-dimethoxy-quinazolin-2-yl)-methyl-amino]-methyl}-3',4',5',6'-tetrahydro-2'H-[2,4']bipyridinyl-1'-yl)-2-methyl-propan-1-one 63, MS: 478 (M⁺);

1-(4'-{[(4-Amino-6,7-dimethoxy-quinazolin-2-yl)-methyl-amino]-methyl}-3',4',5',6'-tetrahydro-2'H-[2,4']bipyridinyl-1'-yl)-ethanone 64, MS: 450 (M⁺);

1-(4'-{[(4-Amino-6,7-dimethoxy-quinazolin-2-yl)-methyl-amino]-methyl}-3',4',5',6'-tetrahydro-2'H-[2,4']bipyridinyl-1'-yl)-butan-1-one 65, MS: 478 (M⁺);

1-(4'-{[(4-Amino-6,7-dimethoxy-quinazolin-2-yl)-methyl-amino]-methyl}-3',4',5',6'-tetrahydro-2'H-[2,4']bipyridinyl-1'-yl)-2,2-dimethyl-propan-1-one 66, MS: 492 (M⁺);

1-(4'-{[(4-Amino-6,7-dimethoxy-quinazolin-2-yl)-methyl-amino]-methyl}-3',4',5',6'-tetrahydro-2'H-[2,4']bipyridinyl-l'-yl)-1-phenyl-methanone 67, MS: 512 (M⁺);

1-(4-{[(4-Amino-6,7-dimethoxy-quinazolin-2-yl)-methyl-amino]-methyl}-4-phenyl-piperidin-1-yl)-2-cyclopropyl-ethanone 68, MS: 490 ([M+H]⁺);

1-(4-{[(4-Amino-6,7-dimethoxy-quinazolin-2-yl)-methyl-amino]-methyl}-4-phenyl-piperidin-1-yl)-1-cyclopentyl-methanone 69, MS: 504 ([M+H]⁺);

1-(4-{[(4-Amino-6,7-dimethoxy-quinazolin-2-yl)-methyl-amino]-methyl}-4-phenyl-piperidin-1-yl)-1-cyclobutyl-methanone 70, MS: 490 ([M+H]⁺);

1-(4-{[(4-Amino-6,7-dimethoxy-quinazolin-2-yl)-methyl-amino]-methyl}-4-phenyl-piperidin-1-yl)-1-cyclopropyl-methanone 71, MS: 476 ([M+H]⁺);

1-[4-{[(4-Amino-6,7-dimethoxy-quinazolin-2-yl)-methyl-amino]-methyl}-4-(2-methoxy-phenyl)-piperidin-1-yl]-butan-1-one 72, MS: 507 (M⁺);

1-[4-{[(4-Amino-6,7-dimethoxy-quinazolin-2-yl)-methyl-amino]-methyl}-4-(4-methoxy-phenyl)-piperidin-1-yl]-butan-1-one 73, MS: 508 ([M+H]⁺);

1-[4-{[(4-Amino-6,7-dimethoxy-quinazolin-2-yl)-methyl-amino]-methyl}-4-(4-methoxy-phenyl)-piperidin-1-yl]-1-cyclopropyl-methanone 74, MS: 506 ([M+H]⁺);or 1-(4-{[(4-Amino-6,7-dimethoxy-quinazolin-2-yl)-methyl-amino]-methyl}-4-thiophen-2-yl-piperidin-1-yl)-butan-1-one 75, MS: 507 (M⁺).

Example 4

6,7-Dimethoxy-N²-methyl-N²-[4-phenyl-1-(propane-2-sulfonyl)-piperidin-4-ylmethyl]-quinazoline-2,4-diamine 13

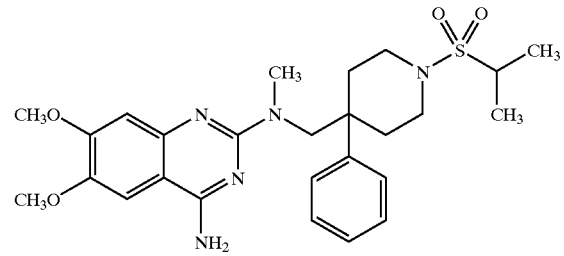

To a solution of 6,7-dimethoxy-N²-(4-phenyl-piperidin-4-ylmethyl)-N²-methyl-quinazoline-2,4-diamine 11 (250 mg) in 20 ml of dichloromethane containing 250 μl of triethylamine was added dropwise with stirring a solution of 70 μl of isopropylsulfonyl chloride in 7 ml of dichloromethane. After stirring at room temperature for two hours, the reaction mixture was worked up and the crude product was subjected to flash chromatography. The resulting 6,7-dimethoxy-N²-methyl-N²-[4-phenyl-1-(propane-2-sulfonyl)-piperidin-4-ylmethyl]-quinazoline-2,4-diamine 13, MS: 514 ([M+H]⁺), was converted into the hydrochloride salt, which crystallized from ethanol/ether to furnish 300 mg as pale yellow crystals.

Similarly, following the procedure described in Example 4, but replacing isopropylsulfonyl chloride with other appropriate sulfonyl chlorides, optionally replacing 6,7-dimethoxy-N²-(4-phenyl-piperidin-4-ylmethyl)-N²-methyl-quinazoline-2,4-diamine 11 with quinazolines from Example 2, and utilizing the modifications known to those skilled in the art, the additional compounds of the general Formula (I) wherein A is —S(O)₂R³ were prepared:

N²-(1-Methanesulfonyl-4-phenyl-piperidin-4-ylmethyl)-6,7-dimethoxy-N²-methyl-quinazoline-2,4-diamine 76, MS: 514 ([M+H]⁻);

N²-(1-Ethanesulfonyl-4-phenyl-piperidin-4-ylmethyl)-6,7-dimethoxy-N²-methyl-quinazoline-2,4-diamine 77, MS: 500 ([M+H]⁺);

6,7-Dimethoxy-N²-methyl-N²-[4-phenyl-1-(propane-1-sulfonyl)-piperidin-4-ylmethyl]-quinazoline-2,4-diamine 78, MS: 514 ([M+H]⁺);

N²-(1'-Methanesulfonyl-2',3',5',6'-tetrahydro-1'H-[2,4']bipyridinyl-4'-yl 79, MS: 486 ([M+H]⁺);

6,7-Dimethoxy-N²-methyl-N²-[1'-(propane-1-sulfonyl)-2',3',5',6'-tetrahydro-1'H-[2,4']bipyridinyl-4'-ylmethyl]-quinazoline-2,4-diamine 80, MS: 514 ([M+H]⁺);

6,7-Dimethoxy-N²-methyl-N²-[1'-(propane-2-sulfonyl)-2',3',5',6'-tetrahydro-1'H-[2,4']bipyridinyl-4'-ylmethyl]-quinazoline-2,4-diamine 81, MS: 514 ([M+H]⁺);

N²-Ethanesulfonyl-2',3',5',6'-tetrahydro-1'H-[2,4']bipyridinyl-4'-ylmethyl)-6,7-dimethoxy-N²-methyl-quinazoline-2,4-diamine 82, MS: 500 ([M+H]⁺); or N²-(1-Cyclopropanesulfonyl-4-phenyl-piperidin-4-ylmethyl)-6,7-dimethoxy-N²-methyl-quinazoline-2,4-diamine 83, MS: 512 ([M+H]⁺).

Example 5

1-(4-{[(4-Amino-6,7-dimethoxy-quinazolin-2-yl)-methyl-amino]-methyl}-4-phenyl-piperidin-1-yl)-1-(tetrahydro-furan-2yl)-methanone 14

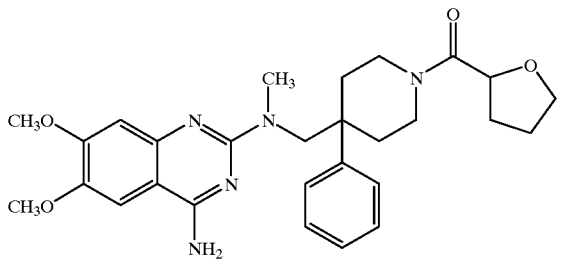

To a solution of 6,7-dimethoxy-N²-(4-phenyl-piperidin-4-ylmethyl)-N²-methyl-quinazoline-2,4-diamine 11 (210 mg), tetrahydro-2-furoic acid (70 mg) and triethylamine (180 μL) in dichloromethane was added BOP reagent (benzotriazol-1-yloxy-tris(dimethylamino)phosphonium hexafluorophosphate) (250 mg). The mixture was stirred at room temperature for 20 hours, evaporated to dryness, and distributed between ethyl acetate and water. The organic phase was washed with sodium bicarbonate, brine, and dried over sodium sulfate. The crude product was purified by flash chromatography to provide 1-(4-{[(4-Amino-6,7-dimethoxy-quinazolin-2-yl)-methyl-amino]-methyl}-4-phenyl-piperidin-1-yl)-1-(tetrahydro-furan-2-yl)-methanone 14, MS: 506 ([M+H]⁺), which was converted into the HCl salt: 180 mg as white crystals.

Similarly, following the procedure described in Example 5, but replacing tetrahydro-2-furoic acid with other appropriate acids, optionally replacing 6,7-dimethoxy-N²-(4-phenyl-piperidin-4-ylmethyl)-N²-methyl-quinazoline-2,4-diamine 11 with quinazolines from Example 2, and utilizing the modifications known to those skilled in the art, the additional compounds of the general Formula (I) wherein A is —C(O)R³ were prepared:

Acetic acid 2-(4-{[(4-amino-6,7-dimethoxy-quinazolin-2-yl)-methyl-amino]-methyl}-4-phenyl-piperidin-1-yl)-1,1-dimethyl-2-oxo-ethyl ester 84, MS: 536 ([M+H]⁺);

1-(4-{[(4-Amino-6,7-dimethoxy-quinazolin-2-yl)-methyl-amino]-methyl}-4-phenyl-piperidin-1-yl)-2-methoxy-ethanone 85, MS: 480 ([M+H]⁺);

1-(4-{[(4-Amino-6,7-dimethoxy-quinazolin-2-yl)-methyl-amino]-methyl}-4-phenyl-piperidin-1-yl)-1-morpholin-4-yl-methanone 86, MS: 521 ([M+H]⁺);

1-(4-{[(4-Amino-6,7-dimethoxy-quinazolin-2-yl)-methyl-amino]-methyl}-4-phenyl-piperidin-1-yl)-2-hydroxy-2-methyl-propan-1-one 87, MS: 494 ([M+H]⁺);

1-(4'-{[(4-Amino-6,7-dimethoxy-quinazolin-2-yl)-methyl-amino]-methyl}-3',4',5',6'-tetrahydro-2'H-[2,4']bipyridinyl-1'-yl)-1-pyridin-3-yl-methanone 88, MS: 513 (M⁺);

3-Amino-1-(4-{[(4-amino-6,7-dimethoxy-quinazolin-2-yl)-methyl-amino]-methyl}-4-phenyl-piperidin-1-yl)-propan-1-one 89, MS: 478 (M⁺);

1-(4-{[(4-Amino-6,7-dimethoxy-quinazolin-2-yl)-methyl-amino]-methyl}-4-phenyl-piperidin-1-yl)-2-methylamino-ethanone 90, MS: 479 ([M+H]⁺);

1-(4-{[(4-Amino-6,7-dimethoxy-quinazolin-2-yl)-methyl-amino]-methyl}-4-phenyl-piperidin-1-yl)-3-hydroxy-butan-1-one 91, MS: 494 ([M+H]⁺);

2-Amino-1-(4-{[(4-amino-6,7-dimethoxy-quinazolin-2-yl)-methyl-amino]-methyl}-4-phenyl-piperidin-1-yl)-ethanone 92, MS: 465 ([M+H]⁺);

1-(4-{[(4-Amino-6,7-dimethoxy-quinazolin-2-yl)-methyl-amino]-methyl}-4-phenyl-piperidin-1-yl)-4,4,4-trifluoro-butan-1-one 93, MS: 532 ([M+H]⁺);

1-(4-{[(4-Amino-6,7-dimethoxy-quinazolin-2-yl)-methyl-amino]-methyl}-4-phenyl-piperidin-1-yl)-1-(tetrahydro-pyran-4-yl)-methanone 94, MS: 520 ([M+H]⁺);

1-(4-{[(4-Amino-6,7-dimethoxy-quinazolin-2-yl)-methyl-amino]-methyl}-4-phenyl-piperidin-1-yl)-1-pyridin-2-yl-methanone 95, MS: 513 ([M+H]⁺);

1-(4-{[(4-Amino-6,7-dimethoxy-quinazolin-2-yl)-methyl-amino]-methyl}-4-phenyl-piperidin-1-yl)-1-pyrrolidin-2-yl-methanone 96, MS: 505 ([M+H]⁺);

2-Amino-1-(4-{[(4-amino-6,7-dimethoxy-quinazolin-2-yl)-methyl-amino]-methyl}-4-phenyl-piperidin-1-yl)-3-phenyl-propan-1-one 97, MS: 555 ([M+H]⁺);

1-(4-{[(4-Amino-6,7-dimethoxy-quinazolin-2-yl)-methyl-amino]-methyl}-4-phenyl-piperidin-1-yl)-4-hydroxy-butan-1-one 98, MS: 494([M+H]⁺);

1-(4-{[(4-Amino-6,7-dimethoxy-quinazolin-2-yl)-methyl-amino]-methyl}-4-phenyl-piperidin-1-yl)-1-(tetrahydro-furan-3-yl)-methanone 99, MS: 505 (M⁺);

1-(4-{[(4-Amino-6,7-dimethoxy-quinazolin-2-yl)-methyl-amino]-methyl}-4-phenyl-piperidin-1-yl)-butane-1,3-dione 100, MS: 528 (M⁺);

1-(4-{[(4-Amino-6,7-dimethoxy-quinazolin-2-yl)-methyl-amino]-methyl}-4-phenyl-piperidin-1-yl)-3-methyl-butan-1-one 101, MS: 491 (M⁺);

1-(4-{[(4-Amino-6,7-dimethoxy-quinazolin-2-yl)-methyl-amino]-methyl}-4-phenyl-piperidin-1-yl)-2-hydroxy-ethanone 102, MS: 465 (M⁺);

1-(4-{[(4-Amino-6,7-dimethoxy-quinazolin-2-yl)-methyl-amino]-methyl}-4-phenyl-piperidin-1-yl)-1-(S)-tetrahydro-furan-2-yl-methanone 103, MS: 505 (M⁺);

1-(4-{[(4-Amino-6,7-dimethoxy-quinazolin-2-yl)-methyl-amino]-methyl}-4-phenyl-piperidin-1-yl)-1-(R)-tetrahydro-furan-2-yl-methanone 104, MS: 505 (M$^+$);

1-(4-{[(4-Amino-6,7-dimethoxy-quinazolin-2-yl)-methyl-amino]-methyl}-4-phenyl-piperidin-1-yl)-1-(R)-pyrrolidin-2-yl-methanone 105, MS: 504 (M$^+$);

1-(4-{[(4-Amino-6,7-dimethoxy-quinazolin-2-yl)-methyl-amino]-methyl}-4-phenyl-piperidin-1-yl)-1-(S)-pyrrolidin-2-yl-methanone 106, MS: 504 (M$^+$);

1-(4-{[(4-Amino-6,7-dimethoxy-quinazolin-2-yl)-methyl-amino]-methyl}-4-phenyl-piperidin-1-yl)-3-hydroxy-propan-1-one 107, MS: 480 ([M+H]$^+$);

1-(4-{[(4-Amino-6,7-dimethoxy-quinazolin-2-yl)-methyl-amino]-methyl}-4-phenyl-piperidin-1-yl)-3-hydroxy-3-methyl-butan-1-one 108, MS: 507 (M$^+$);

1-(4-{[(4-Amino-6,7-dimethoxy-quinazolin-2-yl)-methyl-amino]-methyl}-4-phenyl-piperidin-1-yl)-3-hydroxy-2,2-dimethyl-propan-1-one 109, MS: 507 (M$^+$);

3-Amino-1-(4-{[(4-amino-6,7-dimethoxy-quinazolin-2-yl)-methyl-amino]-methyl}-4-phenyl-piperidin-1-yl)-3-methyl-butan-1-one 110, MS: 507 ([M+H]$^+$);

[3-(4-{[(4-Amino-6,7-dimethoxy-quinazolin-2-yl)-methyl-amino]-methyl}-4-phenyl-piperidin-1-yl)-1,1-dimethyl-3-oxo-propyl]-carbamic acid tert-butyl ester 111, MS: 607 ([M+H]$^+$);

1-(4-{[(4-Amino-6,7-dimethoxy-quinazolin-2-yl)-methyl-amino]-methyl}-4-phenyl-piperidin-1-yl)-1-(4,5-dihydro-1H-imidazol-2-yl)-methanone 112, MS: 504 ([M+H]$^+$);

(S)-1-(4-{[(4-Amino-6,7-dimethoxy-quinazolin-2-yl)-methyl-amino]-methyl}-4-phenyl-piperidin-1-yl)-3-hydroxy-butan-1-one 113, MS: 504 ([M+H]$^+$);

1-(4-{[(4-Amino-6,7-dimethoxy-quinazolin-2-yl)-methyl-amino]-methyl}-4-phenyl-piperidin-1-yl)-1-(2,3-dihydro-benzo[1,4]dioxin-2-yl)-methanone 132; MS: 570 ([M+H]$^+$);

1-(4-{[(4-Amino-6,7-dimethoxy-quinazolin-2-yl)-methyl-amino]-methyl}-4-phenyl-piperidin-1-yl)-2-pyridin-2-yl-ethanone 145, MS: 527 ([M+H]$^+$); or (R)-1-(4-{[(4-Amino-6,7-dimethoxy-quinazolin-2-yl)-methyl-amino]-methyl}-4-phenyl-piperidin-1-yl)-3-hydroxy-butan-1-one 114, MS: 494 ([M+H]$^+$).

Example 6

4-{[(4-Amino-6,7-dimethoxy-quinazolin-2-yl)-methyl-amino]-methyl}-4-phenyl-piperidine-1-carboxylic acid pyridin-3-ylamide 15

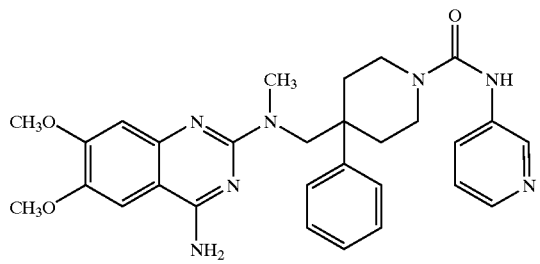

To a solution of 6,7-dimethoxy-N$^2$-(4-phenyl-piperidin-4-ylmethyl)-N$^2$-methyl-quinazoline-2,4-diamine 11 (340 mg) in dichloromethane (5 mL) was slowly added dropwise with stirring a dilute solution of 3-pyridylisocyanate in toluene. The progress of the reaction was monitored by TLC. After completion of the reaction, aq. sodium carbonate was added and the mixture was extracted with dichloromethane. The extract was washed with water, dried over magnesium sulfate, and evaporated. The residue was chromatographed on silica gel to yield 4-{[(4-Amino-6,7-dimethoxy-quinazolin-2-yl)-methyl-amino]-methyl}-4-phenyl-piperidine-1-carboxylic acid pyridin-3-ylamide 15, MS: 528 ([M+H]$^+$). Treatment of the product with HCl in methanol/ethyl acetate gave 242 mg of the hydrochloride salt.

Similarly, following the procedure described in Example 6, but replacing 3-pyridylisocyanate with other appropriate isocyanates, optionally replacing 6,7-dimethoxy-N$^2$-(4-phenyl-piperidin-4-ylmethyl)-N$^2$-methyl-quinazoline-2,4-diamine 11 with quinazolines from Example 2, and utilizing the modifications known to those skilled in the art, the additional compounds of the general Formula (I) wherein A is —C(O)N R$^4$R$^5$ were prepared:

4-{[(4-Amino-6,7-dimethoxy-quinazolin-2-yl)-methyl-amino]-methyl}-4-phenyl-piperidine-1-carboxylic acid dimethylamide 115; MS: 479 ([M+H]$^+$);

4-{[(4-Amino-6,7-dimethoxy-quinazolin-2-yl)-methyl-amino]-methyl}-4-phenyl-piperidine-1-carboxylic acid methylamide 116, MS: 465 ([M+H]$^+$);

4-{[(4-Amino-6,7-dimethoxy-quinazolin-2-yl)-methyl-amino]-methyl}-4-phenyl-piperidine-1-carboxylic acid tert-butylamide 117, MS: 507 ([M+H]$^+$);

4-{[(4-Amino-6,7-dimethoxy-quinazolin-2-yl)-methyl-amino]-methyl}-4-phenyl-piperidine-1-carboxylic acid phenylamide 118, MS: 527 ([M+H]$^+$);

4-{[(4-Amino-6,7-dimethoxy-quinazolin-2-yl)-methyl-amino]-methyl}-4-phenyl-piperidine-1-carboxylic acid butylamide 119, MS: 507 ([M+H]$^+$);

4-{[(4-Amino-6,7-dimethoxy-quinazolin-2-yl)-methyl-amino]-methyl}-4-morpholin-4-yl-piperidine-1-carboxylic acid phenylamide 120, MS: 536 ([M+H]$^+$);

4'-{[(4-Amino-6,7-dimethoxy-quinazolin-2-yl)-methyl-amino]-methyl}-3',4',5',6'-tetrahydro-2'H-[3,4']bipyridinyl-1'-carboxylic acid phenylamide 121, MS: 528 ([M+H]$^+$);

4'-{[(4-Amino-6,7-dimethoxy-quinazolin-2-yl)-methyl-amino]-methyl}-3',4',5',6'-tetrahydro-2'H-[2,4']bipyridinyl-1'-carboxylic acid propylamide 122, MS: 493 (M$^+$);

4'-{[(4-Amino-6,7-dimethoxy-quinazolin-2-yl)-methyl-amino]-methyl}-3',4',5',6'-tetrahydro-2'H-[2,4']bipyridinyl-1'-carboxylic acid tert-butylamide 123, MS: 507 (M$^+$);

4'-{[(4-Amino-6,7-dimethoxy-quinazolin-2-yl)-methyl-amino]-methyl}-3',4',5',6'-tetrahydro-2'H-[2,4']bipyridinyl-1'-carboxylic acid isopropylamide 124, MS: 493 (M$^+$);

4'-{[(4-Amino-6,7-dimethoxy-quinazolin-2-yl)-methyl-amino]-methyl}-3',4',5',6'-tetrahydro-2'H-[2,4']bipyridinyl-1'-carboxylic acid ethylamide 125, MS: 479 (M$^+$);

4'-{[(4-Amino-6,7-dimethoxy-quinazolin-2-yl)-methyl-amino]-methyl}-3',4',5',6'-tetrahydro-2'H-[2,4']bipyridinyl-1'-carboxylic acid butylamide 126, MS: 507 (M$^+$);

4'-{[(4-Amino-6,7-dimethoxy-quinazolin-2-yl)-methyl-amino]-methyl}-3',4',5',6'-tetrahydro-2'H-[2,4']bipyridinyl-1'-carboxylic acid phenylamide 127, MS: 527 (M$^+$);

4'-{[(4-Amino-6,7-dimethoxy-quinazolin-2-yl)-methyl-amino]-methyl}-3',4',5',6'-tetrahydro-2'H-[2,4']bipyridinyl-1'-carboxylic acid (3-fluoro-phenyl)-amide 128, MS: 545 (M$^+$);

4-{[(4-Amino-6,7-dimethoxy-quinazolin-2-yl)-methyl-amino]-methyl}-4-(4-fluoro-phenyl)-piperidine-1-carboxylic acid pyridin-3-ylamide 129 MS: 546 ([M+H]$^+$);

4-{[(4-Amino-6,7-dimethoxy-quinazolin-2-yl)-methyl-amino]-methyl}-4-phenyl-piperidine-1-carboxylic acid pyridin-2-ylamide 130, MS: 528 ([M+H]$^+$); or 1-(4-{[(4-Amino-6,7-dimethoxy-quinazolin-2-yl)-methyl-amino]-methyl}-4-phenyl-piperidin-1-yl)-1-(4-methyl-piperazin-1-yl)-methanone 131, MS: 534 ([M+H]$^+$).

Example 7

$N^2$-[1-(2,3-Dihydro-benzo[1,4]dioxin-6-ylmethyl)-4-phenyl-piperidin-4-ylmethyl]-6,7-dimethoxy-$N^2$-methyl-quinazoline-2,4-diamine 16

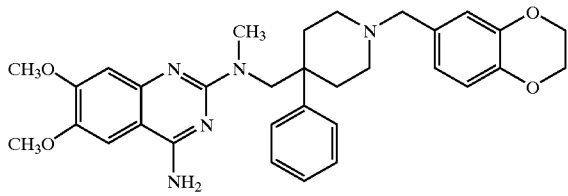

To a solution of 6,7-dimethoxy-$N^2$-(4-phenyl-piperidin-4-ylmethyl)-$N^2$-methyl-quinazoline-2,4-diamine 11 (250 mg) and 1,4-benzodioxan-6-carboxaldehyde (105 mg) in 1,2-dichloroethane (5 ml) was added sodium triacetoxyborohydride (140 mg) in one portion. The mixture was stirred at room temperature for two days. Aqueous NaOH (1N, 5 ml) was added and stirring was continued for one hour. The product was isolated by extraction with dichloromethane and purified by flash chromatograpy, to yield $N^2$-[1-(2,3-Dihydro-benzo[1,4]dioxin-6-ylmethyl)-4-phenyl-piperidin-4-ylmethyl]-6,7-dimethoxy-$N^2$-methyl-quinazoline-2,4-diamine 16, MS: 556 ([M+H]$^+$). Treatment of the product with HCl in methanol/ethyl acetate gave 320 mg of the dihydrochloride salt.

Similarly, following the procedure described in Example 7, but replacing 1,4-benzodioxan-6-carboxaldehyde with other appropriate carboxaldehydes, optionally replacing 6,7-dimethoxy-$N^2$-(4-phenyl-piperidin-4-ylmethyl)-$N^2$-methyl-quinazoline-2,4-diamine 11 with quinazolines from Example 2, and utilizing the modifications known to those skilled in the art, the additional compounds of the general Formula (I) wherein A is —(CH$_2$)$_{0-1}$R$^3$ were prepared:

$N^2$-[1-(2,5-Dimethyl-benzyl)-4-phenyl-piperidin-4-ylmethyl]-6,7-dimethoxy-$N^2$-methyl-quinazoline-2,4-diamine 133, MS: 526 ([M+H]$^+$);

$N^2$-[1-(2,4-Dimethyl-benzyl)-4-phenyl-piperidin-4-ylmethyl]-6,7-dimethoxy-$N^2$-methyl-quinazoline-2,4-diamine 134, MS: 526 ([M+H]$^+$);

$N^2$-[1-(3-Chloro-benzyl)-4-phenyl-piperidin-4-ylmethyl]-6,7-dimethoxy-$N^2$-methyl-quinazoline-2,4-diamine 135 MS: 533 ([M+H]$^+$);

$N^2$-[1-(3,5-Dimethoxy-benzyl)-4-phenyl-piperidin-4-ylmethyl]-6,7-dimethoxy-$N^2$-methyl-quinazoline-2,4-diamine 136, MS: 558 ([M+H]$^+$);

$N^2$-[1-(2-Chloro-benzyl)-4-phenyl-piperidin-4-ylmethyl]-6,7-dimethoxy-$N^2$-methyl-quinazoline-2,4-diamine 137, MS: 533 ([M+H]$^+$);

$N^2$-(1-Cyclohexylmethyl-4-phenyl-piperidin-4-ylmethyl)-6,7-dimethoxy-$N^2$-methyl-quinazoline-2,4-diamine 138, MS: 504 ([M+H]$^+$);

6,7-Dimethoxy-$N^2$-[1-(2-methoxy-benzyl)-4-phenyl-piperidin-4-ylmethyl]-$N^2$-methyl-quinazoline 2,4-diamine 139, MS: 528 ([M+H]$^+$);

6,7-Dimethoxy-$N^2$-methyl-$N^2$-[1-(2-methyl-benzyl)-4-phenyl-piperidin-4-ylmethyl]-quinazoline-2,4-diamine 140, MS: 512([M+H]$^+$);

2-(4-{[(4-Amino-6,7-dimethoxy-quinazolin-2-yl)-methyl-amino]-methyl}-4-phenyl-piperidin-1-ylmethyl)-benzonitrile 141, MS: 523 ([M+H]$^+$);

$N^2$-[1-(2-Ethoxy-benzyl)-4-phenyl-piperidin-4-ylmethyl]-6,7-dimethoxy-$N^2$-methyl-quinazoline-2,4-diamine 142, MS: 542 ([M+H]$^+$);

$N^2$-[1-(2,3-Dihydro-benzo[1,4]dioxin-5-ylmethyl)-4-phenyl-piperidin-4-ylmethyl]-6,7-dimethoxy-$N^2$-methyl-quinazoline-2,4-diamine 143, MS: 556 ([M+H]$^+$);

6,7-Dimethoxy-$N^2$-methyl-$N^2$-[1-(6-methyl-benzo[1,3]dioxol-5-ylmethyl)-4-phenyl-piperidin-4-ylmethyl]-quinazoline-2,4-diamine 144, MS: 556 ([M+H]$^+$);

$N^2$-(1-Cyclopropylmethyl-4-phenyl-piperidin-4-ylmethyl)-6,7-dimethoxy-$N^2$-methyl-quinazoline-2,4-diamine 146, MS: 462 ([M+H]$^+$);

$N^2$-(1-Butyl-4-phenyl-piperidin-4-ylmethyl)-6,7-dimethoxy-$N^2$-methyl-quinazoline-2,4-diamine 147, MS: 464 ([M+H]$^+$); or $N^2$-[1-(1H-Imidazol-2-ylmethyl)-4-phenyl-piperidin-4-ylmethyl]-6,7-dimethoxy-$N^2$-methyl-quinazoline-2,4-diamine 148; MS: 488 ([M+H]$^+$).

Example 8

$N^2$-[1-(1-Imino-butyl)-4-phenyl-piperidin-4-ylmethyl]-6,7-dimethoxy-$N^2$-methyl-quinazoline-2,4-diamine 17

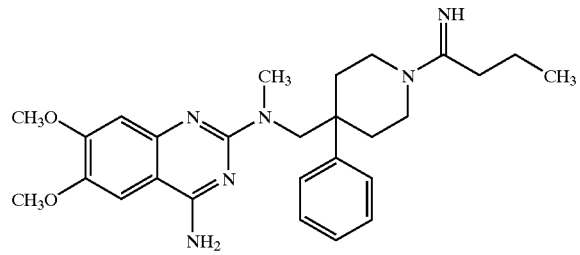

To 6,7-dimethoxy-$N^2$-(4-phenyl-piperidin-4-ylmethyl)-$N^2$-methyl-quinazoline-2,4-diamine 11 (129.8 mg) was added CuCl (31.8 mg), butyronitrile (84 μl), and ethanol (1.0 ml). The reaction mixture was heated in a 90° C. block for one day. Additional CuCl (31.8 mg) and butyronitrile (84 μl) were added and the reaction heated for an additional day. This was chromatographed on silica gel to provide $N^2$-[1-(1-imino-butyl)-4-phenyl-piperidin-4-ylmethyl]-6,7-dimethoxy-$N^2$-methyl-quinazoline-2,4-diamine 17 as indicated by $^1$HNMR and MS: 477 ([M+H]$^+$). This material was further purified by preparative HPLC to afford the corresponding trifluoroacetic acid salt.

Similarly, following the procedure described in Example 8, but replacing butyronitrile with other appropriate nitrites, optionally replacing 6,7-dimethoxy-$N^2$-(4-phenyl-piperidin-4-ylmethyl)-$N^2$-methyl-quinazoline-2,4-diamine 11 with quinazolines from Example 2, and utilizing the modifications known to those skilled in the art, the additional compounds of the general Formula (I) wherein A is —C(NR$^6$)R$^3$ were prepared:

$N^2$-[1-(2-Cyclopropyl-1-imino-ethyl)-4-phenyl-piperidin-4-ylmethyl]-6,7-dimethoxy-$N^2$-methyl-quinazoline-2,4-diamine 149, MS: 489 ([M+H]$^+$); or $N^2$-[1-(1-Cyclobutyl-1-imino-methyl)-4-phenyl-piperidin-4-ylmethyl]-6,7-dimethoxy-$N^2$-methyl-quinazoline-2,4-diamine 150, MS: 489 ([M+H]$^+$).

Example 9

4-{[(4-Amino-6,7-dimethoxy-quinazolin-2-yl)-methyl-amino]-methyl}-N-(3,4-dichloro-phenyl)-4-phenyl-piperidine-1-carboxamidine 18

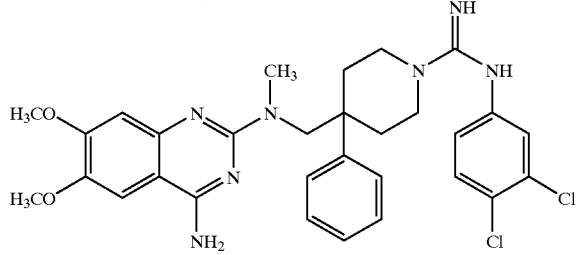

To 1-(3,4-dichlorophenyl)-2-thiourea (66.3 mg, 0.30 mmol) was sequentially added DMF (600 µl), triethylamine (84 µl), and finally a solution of HgCl$_2$ in DMF (0.50 M, 600 µl). A portion of the resulting solution (250 µl) was immediately added to a vial containing 6,7-dimethoxy-N$^2$-(4-phenyl-piperidin-4-ylmethyl)-N$^2$-methyl-quinazoline-2,4-diamine 11 and the mixture was heated in a 55° C. block overnight. After cooling celite® and silica gel were added, and the mixture was filtered through silica gel with CH$_2$Cl$_2$:MeOH:NH$_4$OH, 80:20:5. After removal of solvents the product was further purified by preparative HPLC to afford the corresponding trifluoroacetic acid salt of 4-{[(4-amino-6,7-dimethoxy-quinazolin-2-yl)-methyl-amino]-methyl}-N-(3,4-dichloro-phenyl)-4-phenyl-piperidine-1-carboxamidine 18, MS 595([M+H]$^+$).

Similarly, following the procedure described in Example 9, but replacing 1-(3,4-dichlorophenyl)-2-thiourea with other appropriate thioureas, optionally replacing 6,7-dimethoxy-N$^2$-(4-phenyl-piperidin-4-ylmethyl)-N$^2$-methyl-quinazoline-2,4-diamine 11 with quinazolines from Example 2, and utilizing the modifications known to those skilled in the art, the additional compounds of the general Formula (I) wherein A is —C(NR$^6$)NR$^4$R$^5$ were prepared:

4-{[(4-Amino-6,7-dimethoxy-quinazolin-2-yl)-methyl-amino]-methyl}-4-phenyl-piperidine-N-methyl-N'-cyano-1-carboxamidine 151, MS: 525 (M$^+$);

4-{[(4-Amino-6,7-dimethoxy-quinazolin-2-yl)-methyl-amino]-methyl}-4-phenyl-piperidine-1-carboxylic acid ethylamide 152, MS: 479 ([M+H]$^+$);

4-{[(4-Amino-6,7-dimethoxy-quinazolin-2-yl)-methyl-amino]-methyl}-4-phenyl-piperidine-1-carboxamidine 153, MS: 563 (M$^+$);

4-{[(4-Amino-6,7-dimethoxy-quinazolin-2-yl)-methyl-amino]-methyl}-N-methyl-4-phenyl-piperidine-1-carboxamidine 154, MS: 577 (M$^+$);

4-{[(4-Amino-6,7-dimethoxy-quinazolin-2-yl)-methyl-amino]-methyl}-N-ethyl-4-phenyl-piperidine-1-carboxamidine 155, MS: 477 (M$^+$);

4-{[(4-Amino-6,7-dimethoxy-quinazolin-2-yl)-methyl-amino]-methyl}-4,N-diphenyl-piperidine-1-carboxamidine 156, MS: 525 (M$^+$);

4-{[(4-Amino-6,7-dimethoxy-quinazolin-2-yl)-methyl-amino]-methyl}-N-(4-fluoro-phenyl)-4-phenyl-piperidine-1-carboxamidine 157, MS: 657 (M$^+$);

N$^2$-[1-(1-Imino-1-morpholin-4-yl-methyl)-4-phenyl-piperidin-4-ylmethyl]-6,7-dimethoxy-N$^2$-methyl-quinazoline-2,4-diamine 158, MS: 633 (M$^+$);

N$^2$-[1-(1-Imino-1-pyrrolidin-1-yl-methyl)-4-phenyl-piperidin-4-ylmethyl]-6,7-dimethoxy-N$^2$-methyl-quinazoline-2,4-diamine 159, MS: 504 ([M+H]$^+$);

4-{[(4-Amino-6,7-dimethoxy-quinazolin-2-yl)-methyl-amino]-methyl}-N-(2-ethyl-phenyl)-4-phenyl-piperidine-1-carboxamidine 160, MS: 554 ([M+H]$^+$); or 4-{[(4-Amino-6,7-dimethoxy-quinazolin-2-yl)-methyl-amino]-methyl}-N-(3-chloro-phenyl)-4-phenyl-4-phenyl-piperidine-1-carboxamidine 161, MS: 561 ([M+H]$^+$).

Example 10

4-{[(4-Amino-6,7-dimethoxy-quinazolin-2-yl)-methyl-amino]-methyl}-4-phenyl-piperidine-1-sulfonic acid dimethylamide 19

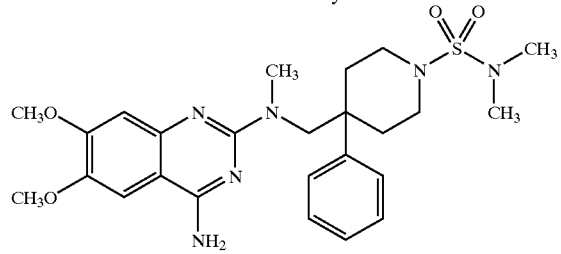

A solution of 6,7-dimethoxy-N$^2$-(4-phenyl-piperidin-4-ylmethyl)-N$^2$-methyl-quinazoline-2,4-diamine 11 (350 mg), dimethylsulfamoyl chloride (140 µl), and triethylamine (240 µl) in tetrahydrofuran (10 ml) was stirred at room temperature for 24 hours. The mixture was diluted with water and extracted with ethyl acetate. The product was chromatographed on silica gel to yield 4-{[(4-Amino-6,7-dimethoxy-quinazolin-2-yl)-methyl-amino]-methyl}-4-phenyl-piperidine-1-sulfonic acid dimethylamide 19, MS: 515 ([M+H]$^+$).

Similarly, following the procedure described in Example 10, but replacing dimethylsulfamoyl chloride with other appropriate sulfamoyl chlorides, optionally replacing 6,7-dimethoxy-N$^2$-(4-phenyl-piperidin-4-ylmethyl)-N$^2$-methyl-quinazoline-2,4-diamine 11 with quinazolines from Example 2, and utilizing the modifications known to those skilled in the art, the additional compound of the general Formula (I) wherein A is —SO$_2$NR$^4$R$^5$ was prepared:

4'-{[(4-Amino-6,7-dimethoxy-quinazolin-2-yl)-methyl-amino]-methyl}-3',4',5',6'-tetrahydro-2'H-[2,4']bipyridinyl-1'-sulfonic acid dimethylamide 162, MS: 515 ([M+H]$^+$).

Example 11

4-{[(4-Amino-6,7-dimethoxy-quinazolin-2-yl)-methyl-amino]-methyl}-4-phenyl-piperidine-1-carboxylic acid ethyl ester 20

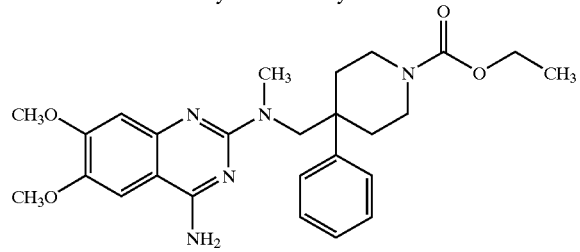

A solution of 6,7-dimethoxy-N$^2$-(4-phenyl-piperidin-4-ylmethyl)-quinazoline-2,4-diamine 11 (375 mg), ethyl chloroformate, and triethylamine (250 µl) in dichloromethane (10 ml) was stirred at room temperature for 24 hours. The mixture was diluted with water and extracted with ethyl acetate. The product was chromatographed on silica gel to yield 4-{[(4-Amino-6,7-dimethoxy-quinazolin-2-yl)-methyl-amino]-methyl}-4-phenyl-piperidine-1-carboxylic acid ethyl ester 20, MS: 479 (M$^+$).

Similarly, following the procedure described in Example 11, but replacing ethyl chloroformate with other appropriate chloroformates, optionally replacing 6,7-dimethoxy-N$^2$-(4-phenyl-piperidin-4-ylmethyl)-N$^2$-methyl-quinazoline-2,4-diamine 11 with quinazolines from Example 2, and utilizing the modifications known to those skilled in the art, the additional compound of the general Formula (I) wherein A is —C(O)OR$^3$ was prepared:

4'-{[(4-Amino-6,7-dimethoxy-quinazolin-2-yl)-methyl-amino]-methyl}-3',4',5',6'-tetrahydro-2'H-[2,4']bipyridinyl-1'-carboxylic acid ethyl ester 163, MS: 480 ([M+H]$^+$).

Example 12

$N^2$-[1-(4,5-Dihydro-1H-imidazol-2-yl)-4-phenyl-piperidin-4-ylmethyl]-6,7-dimethoxy-$N^2$-methyl-quinazoline-2,4-diamine 21

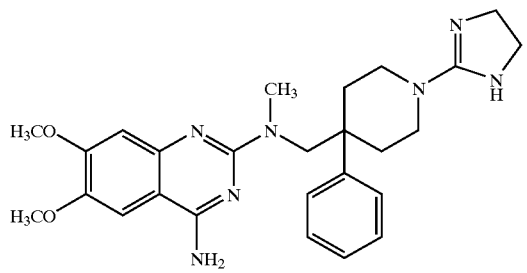

A solution of 6,7-dimethoxy-$N^2$-(4-phenyl-piperidin-4-ylmethyl)-$N^2$-methyl-quinazoline-2,4-diamine 11 (174 mg) and 2-chloroimidazoline hydrogen sulfate (108 mg) in acetonitrile (7.5 ml) was added triethylamine (180 μl). The mixture was stirred at 55° C. for 20 hours. Water (20 ml) was added and the product was extracted into dichloromethane. The product, $N^2$-[1-(4,5-Dihydro-1H-imidazol-2-yl)-4-phenyl-piperidin-4-ylmethyl]-6,7-dimethoxy-$N^2$-methyl-quinazoline-2,4-diamine 21 was isolated as the dihydrochloride salt, MS: 476 ([M+H]$^+$), which crystallized from ethanol/acetone.

Example 13

6,7-Dimethoxy-$N^2$-methyl-$N^2$-(4-phenyl-3,4,5,6-tetrahydro-2H-[1,2']bipyridinyl-4-ylmethyl)-quinazoline-2,4-diamine 22

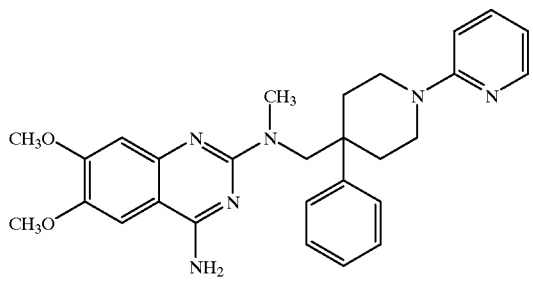

A solution of 6,7-dimethoxy-$N^2$-(4-phenyl-piperidin-4-ylmethyl)-$N^2$-methyl-quinazoline-2,4-diamine 11 (250 mg) and 2-chloropyridine in N-methylpyrrolidone (5 m) was stirred at 130° C. under nitrogen for 48 hours. The cooled reaction mixture was diluted with water and extracted with chloroform. The extract was chromatographed on silica gel to yield 6,7-dimethoxy-$N^2$-methyl-$N^2$-(4-phenyl-3,4,5,6-tetrahydro-2H-[1,2']bipyridinyl-4-ylmethyl)-quinazoline-2, 4-diamine 22, MS: 485 ([M+H]$^+$).

Similarly, following the procedure described in Example 13, but replacing 2-chloropyridine with other appropriate chloropyridines, optionally replacing 6,7-dimethoxy-$N^2$-(4-phenyl-piperidin-4-ylmethyl)-$N^2$-methyl-quinazoline-2,4-diamine 11 with quinazolines from Example 2, and utilizing the modifications known to those skilled in the art, the additional compounds of the general Formula (I) wherein A is heteroaryl were prepared:

4-{[(4-Amino-6,7-dimethoxy-quinazolin-2-yl)-methyl-amino]-methyl}-4-phenyl-3,4,5,6-tetrahydro-2H-[1,2']bipyridinyl-5'-carboxylic acid amide 164, MS: 528 ([M+H]$^+$); or 4-{[(4-Amino-6,7-dimethoxy-quinazolin-2-yl)-methyl-amino]-methyl}-4-phenyl-3,4,5,6-tetrahydro-2H-[1,2']bipyridinyl-3'-carboxylic acid dimethylamide 165, MS: 556 ([M+H]$^+$).

Example 14

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Example 15

| Composition for Oral Administration | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 16

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Example 17

| Parenteral Formulation (IV) | |
| --- | --- |
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 18

| Suppository Formulation | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 19

| Topical Formulation | |
| --- | --- |
| Ingredients | grams |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and additional water is then added q.s. about 100 g.

Example 20

Nasal Spray Formulations

Several aqueous suspensions containing from about 0.025–0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50–100 microliters of formulation per actuation. A typical dosing schedule is 2–4 sprays every 4–12 hours.

Example 21

[$^3$H]prazosin Binding (Alpha-1 Adrenoceptor) Assay

Alpha-1A, alpha-1B, and alpha-1D adrenoceptor transfected CHO-K1 cells, prepared using the methods described in Chang et al., *FEBS Lett* 1998, 422, 279–283, were grown to confluence in T-162 tissue culture flasks in Ham's F-12 culture medium supplemented with 10% fetal bovine serum, geneticin (150 µg/ml) and streptomycin/penicillin (30 µg/mL/30 µg/ml) at 370 in 7% $CO_2$. Cells were harvested by incubating with phosphate-buffered saline (PBS) containing 30 µEDTA for 5–10 min at 37° C. Cells were pelleted by contrifuging at 500×g for 5 min, the pelleted cells were homogenized (Polytron homogenizer) in 10 vols (w/v) of 50 mM Tris, 1 mM EDTA, (homogenisation buffer, pH 7.4 at 4° C.). The homogenate was centrifuged at 45,000×g for 20 min. The pellet was resuspended in 50 mM Tris buffer (pH 7.4 at 4° C.), aliquoted, frozen, and stored at −80° C. for further use.

The membranes were thawed at room temperature and diluted in assay buffer (50 mM Tris buffer at pH 4) at 37° C. for 30 min. The membranes were then filtered over polyethyleneimine-treated GF/B unifilter plates using a Packard Filtermate Harvester and washed with ice-cold 50 mM Tris-HC1, 1 mM EDTA buffer (3×3 sec. Washes). Scintillation cocktail was added to the filter plates and bound radioligand determined by liquid scintillation spectrophotometry.

For each experiment, total binding (in the absence of any test or reference compounds) and non-specific binding (10 µM phentolamine) were determined. For each sample tested, the concentration producing 50% inhibition of binding ($IC_{50}$) and Hill Slope ($n_H$) was determined using iterative non-linear curve fitting techniques with Kaleidagraph (Synergy Software) or other appropriate software. If the radioligand $K_D$ was known, the inhibition dissociation constant ($K_i$) of each ligand was determined according to the method of Cheng and Prusoff (Cheng, Y-C. and Prusoff, W. H., *Biochem. Pharmacol.*, 1973, 22:3099–3108).

Proceeding as in Example 21 compounds of Formula (I) were tested and found to be selective alpha-1B adrenoceptor antagonists.

Example 22

Rat In Vivo, Blood Pressure Assay

Normotensive rats (0.25 to 0.45 kg) are fasted for 18 hours and anesthetized with ether. The right femoral vein is isolated and cannulated with a fluid-filled polyethylene cannula for bolus administration of test substances. The right femoral artery is isolated and cannulated with a fluid-filled polyethylene cannula connected to an external pressure transducer for monitoring mean arterial blood pressure (MAP).

Following cannulation, rats are pretreated (intravenous route) with an angiotensin receptor antagonist, a beta-adrenergic receptor antagonist and an alpha-2 adrenergic receptor antagonist as described in Blue et al., *Br. J. Pharmacol.* (Proceedings Supplement) 1997,120,107P.

The rats are placed in restrainers and allowed to recover from anesthesia. Following a 30-minute period for stabilization, test compound or vehicle are administered, i.v., and blood pressure is monitored continuously for at least 4 hours post-administration.

Proceeding as in Example 22, compounds of Formula (I) were tested and found to be less potent than prazosin at producing blood pressure lowering effects.

Example 23

Radiant Heat Model

Generally, CCI rats are tested for thermal hyperalgesia at least 10 days post-op. The test apparatus consists of an elevated heated (80–82° F.) glass platform. Eight rats at a time, representing all testing groups, are confined individually in inverted plastic cages on the glass floor of the platform at least 15 minutes before testing. A radiant heat source place underneath the glass is aimed at the plantar hind paw of each rat. The application of heat is continued until the paw is withdrawn (withdrawal latency) or the time elapsed is 20 seconds. This trial is also applied to the sham operated leg. Two to four trials are conducted on each paw, alternately, with at least 5 minute interval between trials. The average of these values represents the withdrawal latency.

Proceeding as in Example 23, compounds of Formula (I) were tested and assayed for a significant effect in the radiant heat model assay.

Example 24

Blood Withdrawal Model in Conscious Rat

Short-term maintenance of blood pressure during postural changes, such as on standing—when venous return to the heart is compromised by blood pooling in the lower extremities—is critically dependent on sympathetic vasoconstriction, mediated via alpha1-adrenoceptors. Since clinical use of non-subtype selective alpha1-adrenoceptor antagonists is known to be associated with significant incidence of postural hypotension, this model, in which venous pooling has been mimicked by blood withdrawal, has been used to assess the potential of alpha-1 adrenoceptor antagonists to cause this side effect.

Male Sprague-Dawley Rats (360–540 g) were anesthetized with metofane. An inguinal skin incision was made on the hind limb of the animal. Both left and right femoral arteries and left femoral vein were isolated and cannulated with PE-50 fluid-filled cannulae for measurement of blood pressure, withdrawal of blood and administration of compound, respectively. The incision site was closed using 9 mm auto-clips. Animals were then placed in Bollman cages with their tails secured with masking tape.

Following recovery from anesthesia, a 1 hour stabilization period was allowed. Four ml of blood were then withdrawn into a heparinized syringe, and the effect on blood pressure and heart rate was noted. Five to seven minutes later the blood was returned to the rat. After another 1 hour stabilization period, test compound or vehicle was administered (i.v.). The blood withdrawal procedure was repeated 10 minutes after administration of vehicle or test compound. Blood pressure and heart rate were monitored continuously throughout the experiment using a Gould polygraph (Model MK200A) and Buxco data acquisition computer system. Changes in blood pressure following blood withdrawal were compared before and after dosing with test compound.

Proceeding as in Example 24 compounds of Formula (I) were tested for postural hypotension.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of Formula (I):

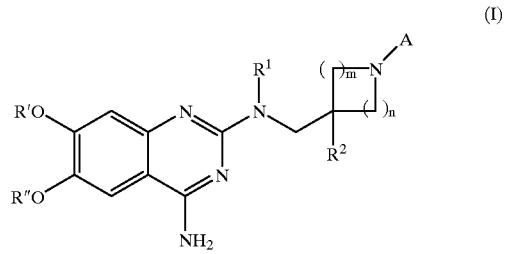

wherein:
$R^1$ is hydrogen or lower alkyl;
$R^2$ is lower alkyl, heterocyclyl, heteroaryl, or aryl, each optionally substituted with lower alkyl, alkoxy, halogen, or cyano;
R' and R" are each independently lower alkyl;
A is hydrogen, $-(CH_2)_{0-1}R^3$, $-C(O)R^3$, $-SO_2R^3$, $-C(O)OR^3$, $-C(O)NR^4R^5$, $-SO_2NR^4R^5$, $-C(NR^6)R^3$, or $-C(NR^6)NR^4R^5$;
$R^3$ is independently in each occurrence lower alkyl optionally substituted with halogen, amino, alkylamino, hydroxy, alkoxy, acyloxy, aminocarbonyl, alkoxycarbonylamino, nitro, or cyano; aryl; arylalkyl; heteroaryl; heteroarylalkyl; cycloalkyl; cycloalkylalkyl; heterocyclyl; or heterocyclylalkyl;
$R^4$ and $R^5$ are each independently from each other hydrogen, or $R^3$ as defined above, or $R^4$ and $R^5$ are taken together with the nitrogen to which they are attached to form a 5- to 7-membered ring, optionally incorporating one or two ring heteroatoms chosen from N, S, or O;
$R^6$ is hydrogen, lower alkyl, or cyano; and
n is an integer from 0 to 2 inclusive, and m is an integer from 0 to 3 inclusive, providing that m+n is equal to or larger than 2;
or an acceptable prodrug, salt, or solvate thereof.
2. The compound of claim 1, wherein $R^2$ is aryl, optionally substituted with lower alkyl, alkoxy, halogen, or cyano.
3. The compound of claim 1, wherein $R^1$ is lower alkyl.
4. The compound of claim 1, wherein $R^1$ is methyl and $R^2$ is phenyl optionally substituted with lower alkyl, alkoxy, halogen, or cyano.
5. The compound of claim 4, wherein A is $-C(O)R^3$.
6. The compound of claim 5, wherein $R^3$ is aryl, heteroaryl, arylalkyl, heteroarylalkyl, or heterocyclyl.
7. The compound of claim 5, wherein $R^3$ is lower alkyl or cycloalkyl.
8. The compound of claim 7, wherein $R^3$ is lower alkyl optionally substituted with fluoro, hydroxy, or alkoxy.
9. The compound of claim 4, wherein A is $-SO_2R^3$.
10. The compound of claim 9, wherein $R^3$ is aryl, heteroaryl, arylalkyl, heteroarylalkyl, or heterocyclyl.
11. The compound of claim 9, wherein $R^3$ is lower alkyl or cycloalkyl.
12. The compound of claim 11, wherein $R^3$ is lower alkyl optionally substituted with fluoro, hydroxy, or alkoxy.
13. The compound of claim 4, wherein A is $-(CH_2)_{0-1}R^3$.
14. The compound of claim 4, wherein A is $-C(O)NR^4R^5$.
15. The compound of claim 4, wherein A is $-SO_2NR^4R^5$.
16. The compound of claim 4, wherein A is $-C(NR^6)R^3$ or $-C(NR^6)NR^4R^5$.
17. The compound of claim 1, wherein the compound is:
1-(4-{[(4-Amino-6,7-dimethoxy-quinazolin-2-yl)-methylamino]-methyl}-4-phenyl-piperidin-1-yl)-1-cyclopropylmethanone;

6,7-Dimethoxy-$N^2$-methyl-$N^2$-[4-phenyl-1-(propane-2-sulfonyl)-piperidin-4-ylmethyl]-quinazoline-2,4-diamine;

1-(4-{[(4-Amino-6,7-dimethoxy-quinazolin-2-yl)-methyl-amino]-methyl}-4-phenyl-piperidin-1-yl)-4,4,4-trifluoro-butan-1-one;

(S)-1-(4-{[(4-Amino-6,7-dimethoxy-quinazolin-2-yl)-methyl-amino]-methyl}-4-phenyl-piperidin-1-yl)-3-hydroxy-butan-1-one;

(R)-1-(4-{[(4-Amino-6,7-dimethoxy-quinazolin-2-yl)-methyl-amino]-methyl}-4-phenyl-piperidin-1-yl)-3-hydroxy-butan-1-one;

1-(4-{[-Amino-6,7-dimethoxy-quinazolin-2-yl)-methyl-amino]-methyl }-4-phenyl-piperidin-1-yl)-1-(tetrahydro-furan-2-yl)-methanone;

1-(4-{[(4-Amino-6,7-dimethoxy-quinazolin-2-yl)-methyl-amino]-methyl}-4-phenyl-piperidin-1-yl)-1-pyrrolidin-2-yl-methanone;

$N^2$-(1-Cyclopropanesulfonyl-4-phenyl-piperidin-4-ylmethyl)-6,7-dimethoxy-$N^2$-methyl-quinazoline-2,4-diamine;

4-{[(4-Amino-6,7-dimethoxy-quinazolin-2-yl)-methyl-amino]-methyl}-4-phenyl-piperidine-1-sulfonic acid dimethylainide;

1-(4-{[(4-Amino-6,7-dimethoxy-quinazolin-2-yl)-methyl-amino]-methyl}-4-phenyl-piperidin-1-yl)-butan-1-one;

1-[4-{[(4-Amino-6,7-dimethoxy-quinazolin-2-yl)-methyl-amino]-methyl}-4-(4-fluoro-phenyl)-piperidin-1-yl]-butan-1-one;

1-(4-{[(4-Amino-6,7-dimethoxy-quinazolin-2-yl)-methyl-amino]-methyl}-4-phenyl-piperidin-1-yl)-1-phenyl-methanone;

4-{[(4-Amino-6,7-dimethoxy-quinazolin-2-yl)-methyl-amino]-methyl}-4-phenyl-piperidine-1-carboxylic acid pyridin-3-ylamide;

$N^2$-[1-(2-Cyclopropyl-1-imino-ethyl)-4-phenyl-piperidin-4-ylmethyl]-6,7-dimethoxy-$N^2$-methyl-quinazoline-2,4-diamine;

4-{[(4-Amino-6,7-dimethoxy-quinazolin-2-yl)-methyl-amino]-methyl }-N-methyl-4-phenyl-piperidine-1-carboxamidine; or $N^2$-[1-(2,3-Dihydro-benzo[1,4]dioxin-6-ylmethyl)-4-phenyl-piperidin-4-ylmethyl]-6,7dimethoxy-$N^2$-methyl-quinazoline-2,4-diamine.

18. A pharmaceutical composition comprising a therapeutically effective amount of the compound of claim 1, in admixture with one or more pharmaceutically acceptable non-toxic carriers.

19. A method of treating a disease state responsive to an alpha-1 adrenoceptor antagonist, the method comprising the step of administering to a subject in need of treatment from said disease state a therapeutically effective amount of the compound of claim 1, wherein the compound is administered as an acceptable prodrug, salt, or solvate thereof.

20. The method of claim 19, wherein the alpha-1 adrenoceptor antagonist is an alpha-1B adrenoceptor antagonist.

21. The method of claim 19, wherein the disease state responsive to an alpha-1 adrenoceptor antagonist is selected from the group consisting of sexual dysfunction, pain, disorders of the urinary tract, and disorders of the central nervous system.

22. The method of claim 20, wherein the disease state responsive to an alpha-1B adrenoceptor antagonist is selected from the group consisting of sexual dysfunction, pain, disorders of the urinary tract, and disorders of the central nervous system.

23. The method of claim 21, wherein the disease state is incontinence, benign prostatic hypertrophy, prostatitis, detrusor hyperreflexia, urinary frequency, nocturia, urinary urgency, overactive bladder, pelvic hypersensitivity, urge incontinence, urethritis, prostatodynia, cystitis, or idiopathic bladder hypersensitivity.

24. The method of claim 22, wherein the disease state is incontinence, benign prostatic hypertrophy, prostatitis, detrusor hyperreflexia, urinary frequency, nocturia, urinary urgency, overactive bladder, pelvic hypersensitivity, urge incontinence, urethritis, prostatodynia, cystitis, or idiopathic bladder hypersensitivity.

25. The method of claim 24, wherein the disease state is benign prostatic hypertrophy or pelvic hypersensitivity.

26. The method of claim 20, wherein the disease state is pain.

27. The method of claim 26, wherein the disease state is inflammatory pain, neuropathic pain, cancer pain, acute pain, chronic pain, or complex regional pain syndromes.

28. The method of claim 20, wherein the disease state is a disorder of the central nervous system.

29. The method of claim 28, wherein the disease state is psychosis, paranoia, schizophrenia, attention deficiency, autism, obsessive or compulsive disorder, anorexia, bulimia, posttraumatic stress disorder, sleep disorder, bipolar disorder, convulsive disorder, depression, mania, seasonal affective disorder, or anxiety.

30. A process for preparing a compound as claimed in claim 1, comprising the step of reacting a compound having a formula

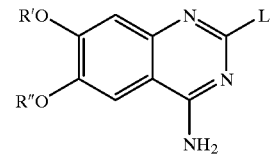

wherein L is a leaving group, and R' and R" are as defined in claim 1, with a compound of general formula

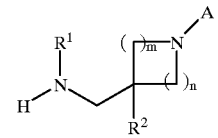

wherein $R^1$, $R^2$, m, n, and A are as defined in claim 1 to provide a compound of Formula (I)

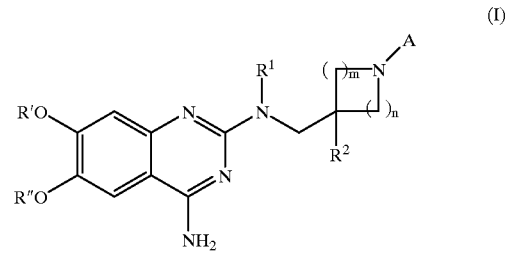

wherein R', R", $R^1$, $R^2$, m, n, and A are as defined in claim 1.

31. A process for preparing a compound as claimed in claim 1, comprising the step of reacting a compound having a formula

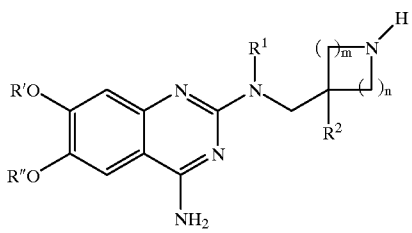

wherein R', R", R¹, R², m, and n are as defined in claim 1, with a compound of the general formula A-L, wherein L is a leaving group and A is as defined in claim 1, to provide a compound of Formula (I)

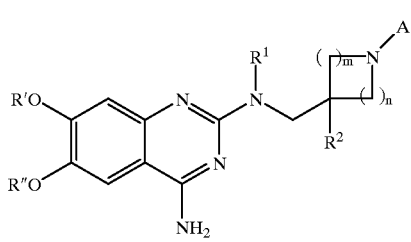

(I)

wherein R', R", R¹, R², m, n, and A are as defined in claim 1.

32. A compound of Formula (I):

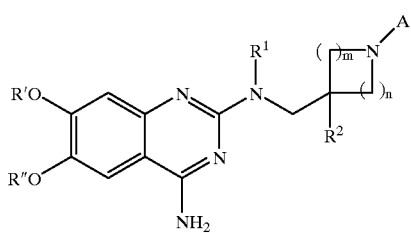

(I)

wherein:

R¹ is hydrogen or lower alkyl;

R² is lower alkyl, heterocyclyl, heteroaryl, or aryl, each optionally substituted with lower alkyl, alkoxy, halogen, or cyano;

R' and R" are each independently lower alkyl;

A is hydrogen, —(CH$_2$)$_{0-1}$R$^3$, —C(O)R$^3$, —SO$_2$R$^3$, —C(O)OR$^3$, —C(O)NR$^4$R$^5$, —SO$_2$NR$^4$R$^5$, —C(NR$^6$)R$^3$, or —C(NR$^6$)NR$^4$R$^5$;

R³ is lower alkyl optionally substituted with halogen, amino, alkylamino, hydroxy, alkoxy, acyloxy, aminocarbonyl, alkoxycarbonylamino, nitro, or cyano; or aryl, arylalkyl, heteroaryl, heteroarylalkyl, cycloalkyl, cycloalkylalkyl, heterocyclyl, or heterocyclylalkyl, each optionally substituted with one or more substituents selected from the group consisting of lower alkyl, halogen, amino, alkylamino, hydroxy, alkoxy, acyloxy, aminocarbonyl, alkoxycarbonylamino, nitro, and cyano; or each optionally substituted with two of said substituents, provided that said substituents are present on adjacent carbons and are taken together with said adjacent carbons to which they are attached to form a 5- to 6-membered ring structure incorporating one or two heteroatoms selected from the group consisting of nitrogen and oxygen;

R⁴ and R⁵ are each independently from each other selected from the group consisting of hydrogen; lower alkyl optionally substituted with halogen, amino, alkylamino, hydroxy, alkoxy, acyloxy, aminocarbonyl, alkoxycarbonylamino, nitro, or cyano; or aryl, arylalkyl, heteroaryl, heteroarylalkyl, cycloalkyl, cycloalkylalkyl, heterocyclyl, or heterocyclylalkyl, each optionally substituted with one or more substituents selected from the group consisting of lower alkyl, halogen, amino, alkylamino, hydroxy, alkoxy, acyloxy, aminocarbonyl, alkoxycarbonylamino, nitro, and cyano; or R⁴ and R⁵ are taken together with the nitrogen to which they are attached to form a 5- to 7-membered heterocyclic ring;

R⁶ is hydrogen, lower alkyl, or cyano; or R⁶ and R⁴ are taken together with the atoms to which they are attached to form an imidazoline ring; and n is an integer from 0 to 2 inclusive, and m is an integer from 0 to 3 inclusive, providing that m+n is equal to or larger than 2;

or an acceptable prodrug, salt, or solvate thereof.

33. The compound of claim 32, wherein R¹ is lower alkyl, and R² is aryl, optionally substituted with lower alkyl, alkoxy, halogen, or cyano.

34. The compound of claim 32, wherein R¹ is methyl and R² is phenyl, optionally substituted with lower alkyl, alkoxy, halogen, or cyano.

35. The compound of claim 34, wherein A is —C(O)R³.

36. The compound of claim 35, wherein R³ is aryl, heteroaryl, arylalkyl, heteroarylalkyl, heterocyclyl, or heterocyclylalkyl, each optionally substituted with one or more substituents selected from the group consisting of lower alkyl, halogen, amino, alkylamino, hydroxy, alkoxy, acyloxy, aminocarbonyl, alkoxycarbonylamino, nitro, and cyano; or each optionally substituted with two of said substituents, provided that said substituents are present on adjacent carbons and are taken together with said adjacent carbons to which they are attached to form a 5- to 6-membered ring structure incorporating one or two heteroatoms selected from the group consisting of nitrogen and oxygen.

37. The compound of claim 35, wherein R³ is lower alkyl or cycloalkyl, each optionally substituted with halogen, amino, alkylamino, hydroxy, alkoxy, acyloxy, aminocarbonyl, alkoxycarbonylamino, nitro, or cyano.

38. The compound of claim 37, wherein R³ is lower alkyl optionally substituted with fluoro, hydroxy, or alkoxy.

39. The compound of claim 34, wherein A is —SO$_2$R³.

40. The compound of claim 39, wherein R³ is aryl, heteroaryl, arylalkyl, heteroarylalkyl, heterocyclyl, or heterocyclylalkyl, each optionally substituted with one or more substituents selected from the group consisting of lower alkyl, halogen, amino, alkylamino, hydroxy, alkoxy, acyloxy, aminocarbonyl, alkoxycarbonylamino, nitro, and cyano; or each optionally substituted with two of said substituents, provided that said substituents are present on adjacent carbons and are taken together with said adjacent carbons to which they are attached to form a 5- to 6-membered ring structure incorporating one or two heteroatoms selected from the group consisting of nitrogen and oxygen.

41. The compound of claim 39, wherein R³ is lower alkyl or cycloalkyl, each optionally substituted with halogen, amino, alkylamino, hydroxy, alkoxy, acyloxy, aminocarbonyl, alkoxycarbonylamino, nitro, or cyano.

42. The compound of claim 41, wherein R³ is lower alkyl optionally substituted with fluoro, hydroxy, or alkoxy.

43. A pharmaceutical composition comprising a therapeutically effective amount of the compound of claim 32, in admixture with one or more pharmaceutically acceptable non-toxic carriers.

44. A process for preparing a compound as claimed in claim 32, comprising the step of reacting a compound having a formula

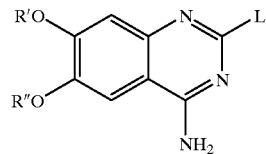

wherein L is a leaving group, and R' and R" are as defined in claim 32, with a compound of general formula

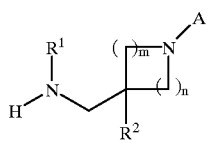

wherein $R^1$, $R^2$, m, n, and A are as defined in claim 32 to provide a compound of Formula (I)

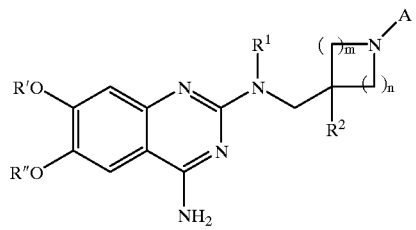

(I)

wherein R', R", $R^1$, $R^2$, m, n, and A are as defined in claim 32.

45. A process for preparing a compound as claimed in claim 32, comprising the step of reacting a compound having a formula

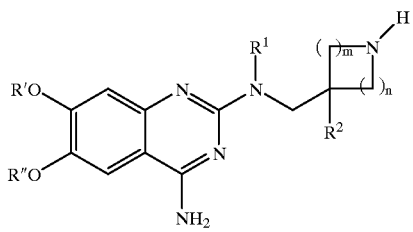

wherein R', R", $R^1$, $R^2$, m, and n are as defined in claim 32, with a compound of the general formula A-L, wherein L is a leaving group and A is as defined in claim 32, to provide a compound of Formula (I)

(I)

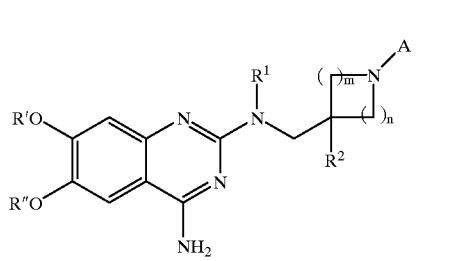

wherein R', R", $R^1$, $R^2$, m, n, and A are as defined in claim 32.

* * * * *